US006004763A

United States Patent [19]
Gengoux et al.

[11] Patent Number: 6,004,763
[45] Date of Patent: Dec. 21, 1999

[54] ANTIGEN-CARRYING MICROPARTICLES AND THEIR USE IN THE INDUCTION OF HUMORAL OR CELLULAR RESPONSES

[75] Inventors: Christine Gengoux, Argenteuil; Claude Leclerc, Paris, both of France

[73] Assignee: Institut Pasteur, France

[21] Appl. No.: 09/076,646

[22] Filed: May 12, 1998

Related U.S. Application Data

[63] Continuation-in-part of application No. 08/397,286, Apr. 28, 1995, Pat. No. 5,871,747.

[30] Foreign Application Priority Data

Sep. 11, 1992 [FR] France ................................. 92 10879

[51] Int. Cl.⁶ .......................... G01N 33/53; A61K 39/21; A61K 39/385; A61K 39/12

[52] U.S. Cl. .................. 435/7.24; 424/208.1; 424/193.1; 424/186.1; 424/188.1; 530/811; 530/815

[58] Field of Search .............................. 424/208.1, 193.1, 424/186.1, 188.1; 530/811, 815; 435/7.24

*Primary Examiner*—Jeffrey Stucker
*Assistant Examiner*—Hankyel T. Park
*Attorney, Agent, or Firm*—Bierman, Muserlian and Lucas

[57] ABSTRACT

The invention concerns the use, in the induction of an immune response, of a synthetic microparticle polymer carrying on the surface one or more covalently bonded proteins capable of carrying one or more epitopes, the molecular weight of the protein(s) on the surface of the microparticles, being adjusted so as to direct the immune response to the induction of a humoral and cellular response or to the induction of a mainly cellular response, said microparticles have an average diameter of approximately 0.25 to 1.5 μm.

23 Claims, 19 Drawing Sheets

6,004,763

SEQUENCE LISTING

<160> NUMBER OF SEQ ID NOS: 5

<210> SEQ ID NO 1
<211> LENGTH: 13
<212> TYPE: PRT
<213> ORGANISM: Hepatitis B virus

<400> SEQUENCE: 1

Met Gln Trp Asn Ser Thr Thr Phe His Gln Thr Leu Gln
 1               5                  10

<210> SEQ ID NO 2
<211> LENGTH: 14
<212> TYPE: PRT
<213> ORGANISM: Hepatitis B virus

<400> SEQUENCE: 2

Gln Asp Pro Arg Val Arg Gly Leu Tyr Phe Pro Ala Gly Gly
 1               5                  10

<210> SEQ ID NO 3
<211> LENGTH: 13
<212> TYPE: PRT
<213> ORGANISM: POLIOMYELITIS VIRUS

<400> SEQUENCE: 3

Lys Leu Phe Ala Val Trp Lys Ile Thr Tyr Lys Asp Thr
 1               5                  10

<210> SEQ ID NO 4
<211> LENGTH: 11
<212> TYPE: PRT
<213> ORGANISM: POLIOMYELITIS VIRUS

<400> SEQUENCE: 4

Asp Asn Pro Ala Ser Thr Thr Asn Lys Asp Lys
 1               5                  10

<210> SEQ ID NO 5
<211> LENGTH: 40
<212> TYPE: PRT
<213> ORGANISM: Human immunodeficiency virus type 1

<400> SEQUENCE: 5

Ile Asn Cys Thr Arg Pro Asn Asn Thr Arg Lys Ser Ile Arg Ile
 1               5                  10                  15

Gln Arg Gly Pro Gly Arg Ala Phe Val Thr Ile Gly Lys Ile Gly Asn
                20                  25                  30

Met Arg Gln Ala His Cys Asn Ile
            35                  40

ANTIGEN-CARRYING MICROPARTICLES AND THEIR USE IN THE INDUCTION OF HUMORAL OR CELLULAR RESPONSES

This application is a continuation-in-part of Ser. No. 08/397,286, filed Apr. 28, 1995 now U.S. Pat. No. 5,871, 747.

The object of the present invention is microparticles carrying antigens on their surface and their use in the induction of humoral or cellular responses.

More specifically the invention also relates to microparticles carrying proteins having specific molecular weights on their surface.

BACKGROUND OF THE INVENTION

The B cells which express immunoglobulin receptors specific for an individual antigen are highly effective for the presentation of this antigen (Rock et al. C., J. Exp. Med. (1984) 160; 1102; Hutchings et al. Eur; j; Immunol. (1987) 17: 393). For example, specific B cells can present tetanus toxin to T cells at antigen concentrations $10^4$ times lower than those required for the presentation by non-specific B cells or peripheral blood monocytes (Lanzavecchia, Nature (1985) 314:537).

In addition, in vivo studies with mice deficient in B cells show that these cells are required for the activation of T cells of lymphatic ganglions (Janeway et al., J. Immunol. (1987) 138:2848; Kurt-Jones et al. A. K. J. Immunol. (1987) 140:3773).

Mice deficient in B cells also show reduced responses with respect to specific $CD4^+$ and $CD8^+$ T cells from tumors, after immunization with Freund's murine leukemia virus (Schultz et al., Science, (1990) 291).

The capacity of B cells to modify and to present the antigen with a view to recognition by $CD4^+$ helper T cells restricted by the class II major histocompatibility complex (MHC) forms the basis of a model for the activation of the B cells by T cells (Noelle et al., The Faseb Journal (1991) 5:2770).

The recognition of the peptide-class II MHC complex by $CD4^+$ helper T cells on the surface of the B cells leads to the formation of physically stable conjugates between the T cells and the B cells (Kupfer et al. S. J., Proc. National acad. Sci. USA (1986) 83:6080).

This direct recognition results in the proliferation and the differentiation of B cells in response to lympholines such as Interleukin-2, Interleukin-4 or Interleukin-5.

The induction of the antibody response against an antigen requires the presentation of the antigen by the B cells.

The majority of the studies on antigen presentation have been carried out using soluble proteins such as tetanus toxoid, lysozyme, hemocyanin (LH). However, most of the antigens to which the immune system is exposed are contained in complex particulate structures such as bacteria or parasites.

It is well known that cells which are capable of phagocytosis such as the macrophages can present bacterial antigens to T cells.

However, it is not known whether cells which do not phagocytose, such as B cells, can present complex antigens of significant size.

It has recently been shown that, in vivo, bacterial antigens must be in a soluble form in order to induce an antibody-dependent response by the T cells (Leclerc et al., J. Immunol. (1990) 144:3174; Leclerc et al., J. Immunol. (1991) 147:3545).

However, it seemed advisable to determine also that, in vivo, bacterial protein antigens are exclusively presented to the T cells by the phagocytic cells and that the B cells cannot modify antigens in particle form.

The study of antigen presentation and the induction of the cellular and/or humoral T response is of particular scientific and medical importance.

In fact, directing the response towards a purely cellular response or a purely humoral response could allow vaccination against certain pathogens, modification of certain biological dysfunctions and curing certain pathologies.

For example, such direction would enable the elimination of persistent infections or the regulation of allergic responses.

In addition, there are two sub-populations of $CD4^+$ T cells, Th1 and Th2, which have different capacities to produce various lymphokines (Mosmann; Cherwinski, Bond, Giedlin and Coffman, J. Immunol., 136, 2348–2357 (1986)). The induction of Th1 or Th2 plays a major role in the resistance to bacterial, parasitic or viral infections. Thus, in the case of murine cutaneous leishmaniasis, the Th1 protect from infection while the Th2 aggravate the disease. In vitro, B lymphocytes optimally stimulate the proliferation of Th2 clones while a strong proliferation of Th1 clones is observed with adherent cells (Gajewski, Pinnas, Wong and Fitch, J. Immunol., 146, 1750–1758 (1991)).

Directing of the antigen towards presentation by the B cells or macrophages could allow induction of Th1 or Th2 responses.

Various techniques have been developed in the past to achieve a better immune response.

The oldest method consists of activating the immune system with adjuvants. Thus, Freund's adjuvant leads to an increased intensity of the humoral and cellular responses. However, such adjuvants have major disadvantages due to their lack of specificity, toxicity, and immunological side-reactions which may be caused by their lack of purity.

The iscomes (immuno-stimulating complexes) are composed of an antigenic complex and an adjuvant, QuilA, which is extracted from trees. These particles have a diameter of about 35 nm and are composed of sub-units of about 12 nm. They lead to the induction of an immune response but more often the antigens are encapsulated and thus then released in the external medium. In addition, the technique does not allow accurate control of the type of cells presenting these particles, and these particles therefore induce a double humoral and cellular response.

Lastly, from a practical standpoint, these particles are difficulty to prepare, lack stability and have significant toxicity.

Liposomes, which have also been tested for use in inducing an immune response, have the same disadvantages as the iscomes.

Biodegradable microparticles such as for example lactic and glutamic acid polymers have also been developed (Aguado and Lambert, Immuno. Biol., 184, 113–125 (1992)). These particles liberate the antigen in a soluble form during their degradation. This liberation enables presentation of the antigen by different cells and the induction of a humoral response without the possibility of direction towards a specifically cellular response.

Particles composed entirely of recombinant proteins have also been synthesized. Thus, French patent application FR 2 635 532 describes particles composed of a hybrid protein between Hbs antigen and an immunogenic sequence presumed to induce neutralizing antibodies directed against the HIV virus.

Particles containing poliomyelitis toxin have also been produced.

These particles have significant disadvantages. Thus, it is very difficult to insert long sequences into these particles. In addition, they induce as much humoral as cellular response and it is thus not possible to obtain specifically one or the other.

Polyacrolein or polystyrene particles to which antibodies have been coupled have already been used for the development of separation techniques (Rembaum et al., Immunol. (1982) 52:341–351).

However, no use for the preparation of vaccines and in vivo immunization has been reported. The beads used have diameters of 20 to 35 nm (polyacrolein) or of 40 to 120 $\mu$m (polystyrene).

Polyacrolein particles of 2 $\mu$m diameter have also been used for the in vitro study of T response stimulation (Ziegler et al., Eur J; Immunol. (1987), 17: 1287–1296). The activity of these beads was not tested in vivo.

Porous microspheres (1 to 1000 $\mu$m) in which the antigens are immobilized inside the micropores by captation or physical coupling have been disclosed by Cahn in U.S. Pat. No. 5,008,116. In this patent the antigen is progressively released in the circulation and is therefore under soluble form.

In all this work, the size of the particles was not considered to be a critical criterion. Moreover, particles of small size (nanoparticles) such as Hbs particles could be presented by B lymphocytes. On the other hand, particles with too large size (greater than 5–10 microns) could not be presented by phagocytic cells.

The various solutions proposed in the prior art, on the one hand to induce a significant immune response and on the other to direct this response specifically towards one of the two response routes, humoral or cellular, are thus not satisfactory.

SUMMARY OF THE INVENTION

The invention offers the development of products giving a good immune response with either a cellular or a humoral direction.

According to the invention, it has been found that such a response can be induced by using microparticles, of small size and having varied antigenic molecular weights.

The present invention particularly relates to synthetic polymer microparticles carrying on their surface at least one covalently bonded proteins, each carrying at least one epitope to induce an humoral or cellular response, the molecular weights of the proteins being adjusted to direct the said immune response towards the induction of cellular or humoral response.

In a preferred embodiment, the molecular weight of the protein is greater than 30 kD, and preferably greater than 50 kD, in which case the immune response is mainly a cellular response.

In another preferred embodiment, the molecular weight of the protein is lower than 30 kD, preferably lower than 15 kD, and the protein comprises B and T epitopes. The immune response is an humoral and cellular response.

The invention also relates to the characteristics below, considered alone or in all technically possible combinations.

The microparticles advantageously have an average diameter of between about 0.25 $\mu$m and 1.5 $\mu$m, and preferentially of about 1 $\mu$m so as to be able to be presented to CD4$^+$ T lymphocytes by phagocytic cells but not by B lymphocytes.

The coupling of the antigenic proteins or microparticles must be covalent in order to avoid the liberation of the antigen in soluble form.

Said microparticles are more particularly characterized in that the covalent bond is formed by reaction between the $NH_2$ and/or CO groups of the proteins and the material making up the microparticle.

Advantageously such bond is created by using a bridging reagent as intermediate, such as for example glutaraldehyde or carbodiimide. However, any other bifunctional reagent able to form such a bond can be used. Such reagents are known, see for example <<Synthetic polypeptides as antigens, M. H. Von Regensmortel, J. P. Briand, S. Muller and S. Plane 1988 (Elsevier)>>. This bond can also be formed without a bridging reagent.

The material of the microparticle can advantageously be a biocompatible polymer, such as an acrylic polymer, for example polyacrolein or polystyrene or the poly(alpha-hydroxy acids), copolymers of lactic and glycolic acids, or lactic acid polymers.

By polymer should be understood any homopolymer or hetero or copolymer.

It must allow covalent bonding of the proteins to the material and must not cause a rejection or toxic reaction by the organism into which it may be injected. Advantageously, for human therapeutic applications, it should be a biodegradable polymer, for example a polymer able to be degraded by cells containing lysosomal enzymes, such as the macrophages.

Such biodegradable materials can include lactic and glutamic acid polymers, starch or polymers used for biomedical applications, and in particular those used-for sutures.

Such microparticles can carry on their surface, in addition to the antigenic proteins, molecules able to activate the immune system, such as the interleukins, in particular gamma-interferon or interleukin 4.

The microparticles which are the object of the present invention can in addition be encapsulated in order to protect the antigens fixed to their surfaces from degradation and to transport them to their site of action.

They can thus comprise a nucleus formed from a polysaccharide matrix, to which are bound the antigens, an initial lipid layer bound covalently to the nucleus and a second layer of amphophilic molecules.

Another object of the invention is drugs or vaccines comprising the microparticles described above, as well as pharmaceutical compositions characterized in that they contain them, in combination with pharmaceutically compatible diluents or adjuvants.

The present invention relates furthermore to a method of inducing an immune response in warm blooded animals comprising administering to these animals an inducing amount of these microparticles.

These microparticles can carry one or more proteins which can themselves each contain one or more epitopes. Such proteins can be glycoproteins, synthetic peptides containing an epitope or several epitopes, or any other nonprotein molecule or molecule containing a protein portion able to induce an immune response.

The proteins and antigens covalently bonded to the microparticles depend on the anticipated application for said microparticles.

They also depend on the type of immune response required, but also on the disease or ailment to be treated or against which the patient is to be protected.

Examples of epitopes which may be used are the epitopes from the Pre S2 region of the HBS antigen of the viral hepatitis virus, with the following sequences:
T epitope: Pre S:T (120–132)
   MQWNSTTFHQTLQ (SEQ ID NO:1)
B epitope: Pre S:B (132–145)
   QDPRVRGLYFPAGG (SEQ ID NO:2)
Other examples are the epitopes of the VP1 protein of the poliomyelitis virus whose sequences are as follows:
T epitope: C3: T (103–115)
   KLFAVWKITYKDT (SEQ ID NO:3)
B epitope: C3: B (93–103)
   DNPASTTNKDK (SEQ ID NO:4)
Another example is the epitope of the V3 loop of the GP120 protein of the HIV1 virus whose sequence is the following:
T+B epitope: V3 loop
   INCTRPNNNTRKSIRIQRG-
   PGRAFVTIGKIGNMRQAHCNI (SEQ ID NO:5)

Such microparticles may be injected into patients who are to be treated in a therapeutic or prophylactic manner in ways known to those skilled in the art, for example by subcutaneous, intra-peritoneal, or intravenous injection or by any other means for inducing an immune response.

This subject is discussed in Current protocols in immunology (edited by J. P. Coligen, A. M. Kruisbeek, D. H. Margulies, E. M. Shevach, W. Strober, published by Wiley-Interscience), in which the range of immunological techniques is listed.

A particular advantage of the present invention rests in the fact that it enables the induction of a humoral or cellular immune response without the addition of adjuvants to the beads or microparticles. However, the addition of non toxic adjuvants not causing an immune side-reaction is also envisageable within the scope of use according to the present invention.

The present invention is illustrated without being in any way restricted by the following examples in which:

BRIEF DESCRIPTION OF THE DRAWINGS

The diagrams of FIG. 1 are the results of fluorimetric analyses (FACS) of microparticles carrying the KLH or TNP-KLH antigens. The ordinates show the antibody used (PBS-control, anti-KLH, anti-TNP). The abscissae show the type of microparticle tested B (KLH), B(TNP-KLH), B (OVA) and B (OVA-TNP) which correspond to the microparticles on which are bonded respectively KHL, TNP-KLH, ovalbumin and ovalbumin-TNP.

FIGS. 2A to 2D show the capacities of spleen and macrophage cells and of TNP-specific B cells activated by LPS to present KLH, TNP-KLH, microparticles carrying KLH and microparticles carrying TNP-KLH.

FIG. 3 is a curve showing the proliferative responses of ganglion cells from mice immunized with soluble lysozyme and stimulated in vitro by soluble lysozyme (FIG. 3A) or by microparticles carrying lysozyme and having diameters of 0.25, 0.75 and 1.5 $\mu$m(FIG. 3B). The cell proliferation was measured by the incorporation of thymidine (CPM) as ordinate, with the microparticle dilution shown on the abscissa.

FIG. 4 shows the production of IL2/IL4 by a lysozyme-specific hybridoma after stimulation by soluble lysozyme (FIG. 4A) or by microparticles carrying lysozyme (FIG. 4B). The microparticle concentrations are shown on the abscissae while the proliferation is shown on the ordinates.

FIGS. 5A and 5B show the activation of the lysozyme-specific T hybridoma measured by the production of IL2/IL4 after stimulation by soluble lysozyme(FIG. 5A) or lysozyme coupled to microparticles (FIG. 5B) in the presence of splenocytes or A20 B cells as cells presenting the antigen.

FIGS. 6A and 6B show the in vitro proliferation after stimulation by soluble lysozyme of inguinal ganglion cells from mice immunized with respectively soluble lysozyme in complete Freund's adjuvant (FIG. 6A) and by lysozyme coupled to microparticles (FIG. 6B).

FIGS. 7A and 7B show the in vitro proliferation after stimulation by lysozyme of inguinal ganglion cells from mice immunized by different concentrations of soluble lysozyme (FIG. 7A) or lysozyme coupled to microparticles (FIG. 7B).

FIG. 8 shows the proliferation of ganglion cells from mice immunized with lysozyme in complete Freund's adjuvant or in PBS or in the presence of microparticles coupled to patella hemocyanin, or KLH (Keyhole Limpet Hemocyanin).

FIG. 9 shows the proliferative response of ganglion cells from mice immunized with soluble hemoglobin in adjuvant (Hb+CFA) or coupled to beads (B-Hb).

FIG. 10 shows the proliferative response of mouse cells stimulated by soluble ovalbumin (OVA+CFA) or ovalbumin coupled to beads (B-OVA).

The proliferative response of the hemoglobin and ovalbumin respectively was measured as ordinate by the incorporated radioactivity (CPM) as a function of the quantity of hemoglobin or ovalbumin (as abscissa) used for restimulating the cells.

FIG. 11 illustrates the proliferation of mouse cells after immunization with the C3 peptide as its soluble form (C3:T+CFA) or as microparticles (B-C3: T). The cells were restimulated in the presence of a quantity of soluble C3 (as abscissa) and the proliferation was measured (ordinate).

FIG. 12 shows the proliferation of mouse cells after immunization with the pre-S:TB peptide as its soluble form (Pre-S:TB+alum) or as microparticles (B-pre-S:TB) or the pre-S:B peptide in particulate form (B-Pre S:B) and restimulated by the Pre-S peptide.

FIGS. 13A and 13B represent respectively the levels of anti-lysozyme antibody (FIG. 13A) and anti-KLH antibody (FIG. 13B) of mice immunized with lysozyme and alum adjuvant, with microparticles carrying lysozyme or with microparticles carrying LH.

FIGS. 14 and 15 show the antibody response of mice immunized with hemoglobin (FIG. 14) or ovalbumin (FIG. 15) in soluble or particulate form. The log of the antibody titer is shown on the ordinate with time on the abscissa.

FIG. 16 shows the antibody response of mice immunized by soluble pre-S: TB peptide, or the pre-S: TB or pre-S: B peptides in particulate forms. The ordinate and the abscissa of this curve are as defined for FIGS. 14 and 15.

FIG. 17 illustrates the comparison of the capacity of five different proteins coupled to synthetic beads to induce antibody responses.

FIGS. 18A and 18B illustrate the kinetics and specificity of the antibody response induced by particulate HEL. The anti HEL response and the anti-LH response are represented respectively on FIGS. 18A and 18B.

FIG. 19 illustrates the IgG1 antibodies induction by particulate HEL.

FIG. 20 illustrates the antibody responses of mice immunized with various doses of soluble or particulate HEL.

FIG. 21 illustrates the abolishment of antibody induction by particulate HEL after in vivo elimination of CD4+ T cells.

EXAMPLE 1

Figure 1:
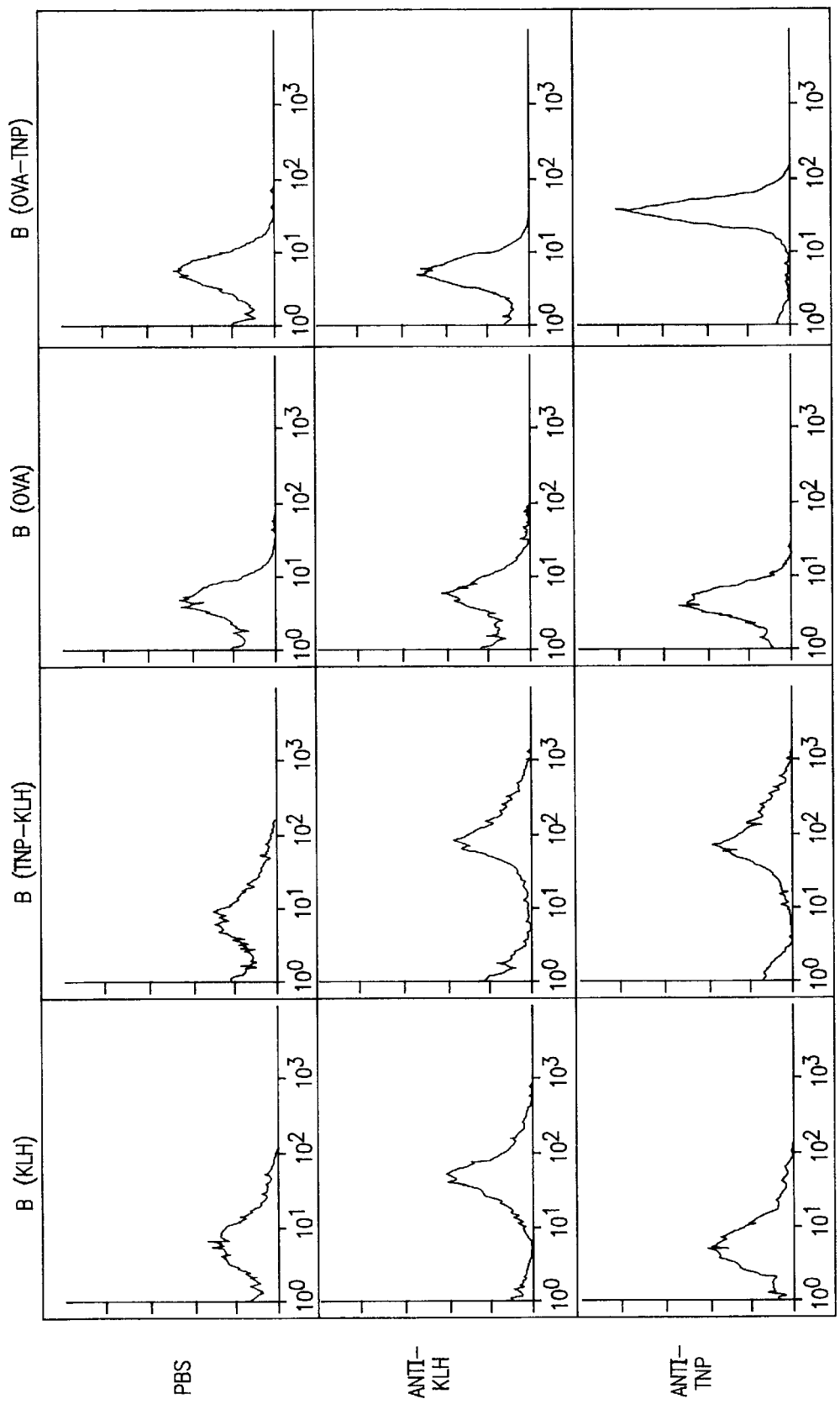
Figure 2A:
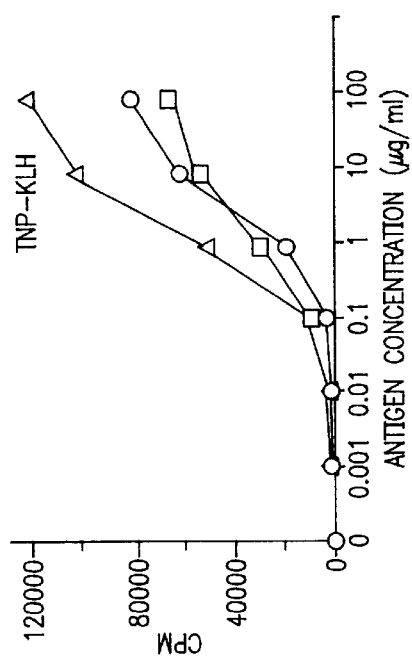
Figure 2B:
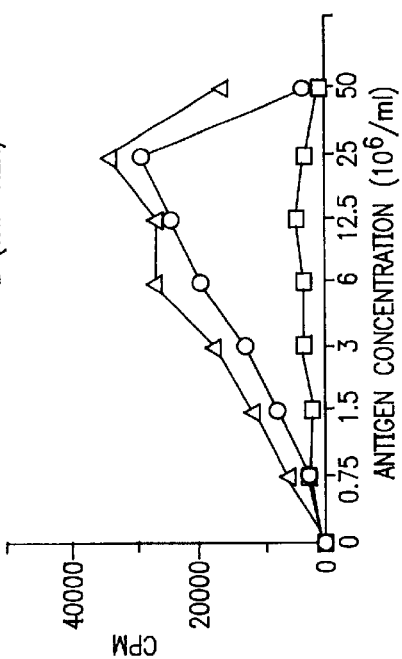
Figure 2C:
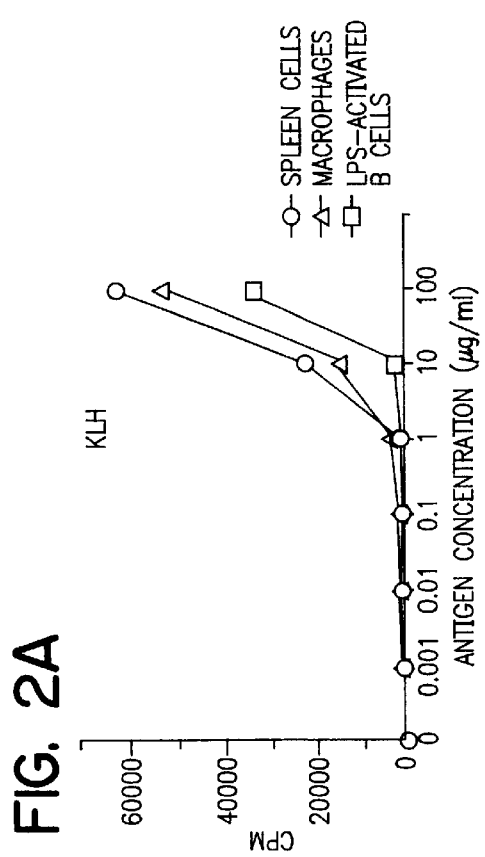
Figure 2D:
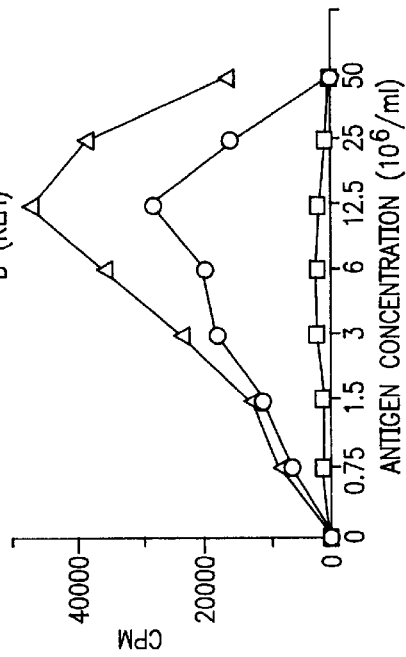

Preparation of beads coupled to KLH or to ovalbumin.

1. Materials and methods and presentation by B cells or by macrophages.

The mice were 6 to 8 weeks old BALB/c and DBA/2 females.

The antigens were KLH and ovalbumin(OVA)marketed by Sigma Chemical (St Louis, USA). The trinitrophenylated hemocyanin (TNP4-KLH) was prepared as previously described (Shutze et al., J. Immunol. (1989) 142:2635).

1.1 Covalent coupling of antigens to poly(acrolein) microparticles.

Poly(acrolein) microparticles with diameter between 0.25 and 1.5 µm, marketed by Polysciences Inc. (Washington Pa.) were coupled to ovalbumin or KLH as previously described (Rembaum et al., Immunol. (1982) 52:341; Ziegler et al., Eur. J. Immunol. (1987) 17:1287).

1 ml of these microparticles was washed twice in PBS and resuspended in 1 ml of KLH or ovalbumin (5 mg/ml in PBS). After 3 hours' incubation at ambient temperature, the microparticles were washed twice in PBS and resuspended in 2 ml of PBS containing 15 of bovine serum albumin (BSA) and antibiotics. The microparticles thus obtained were stored at 4° C. until used.

The microparticles carrying the TNP-OVA or TNP-KLH antigens were prepared by incubation of microparticles carrying OVA or KLH with TNBS (trinitrobenzene sulfonate).

2 ml of the microparticles which had been coupled to KLH or ovalbumin were washed twice in PBS and resuspended in 2 ml of cacodylate buffer containing 10 mg/ml of TNBS. The microparticles were incubated for 30 minutes in darkness at ambient temperature and washed three times in PBS. They were resuspended in 2 ml of PBS containing 1% BSA and antibiotics and stored at 4° C.

1.2 Analysis by flow cytofluorimetry.

50 µl of microparticles were washed twice in PBS containing 1% of BSA and incubated for 40 minutes at 4° C. with mouse anti-KLH or anti-TNP serum. After two washes the microparticles were incubated with goat antibody coupled to FITC (fluoroisothiocyanate) directed against mouse immunoglobulins (Biosys, Compiegne, France) for 40 minutes at 4° C.

After four washes the microparticles were resuspended in 1 ml of PBS containing 1% of BSA.

The fluorescence intensity was measured by use of a FACSAN flow cytometer (Becton Dickinson, Mountain View, Calif.).

1.3 Culture medium.

The lymphocytes were cultured in RPMI 1640 (Seromed, Munich, FRG) complemented with 2 mM L-glutamine, 10% of FCS (fetal calf serum) inactivated by heat, 50 µM of 2-ME and antibiotics.

1.4 Establishment of the KLH-specific Th cell line.

This cell line was established and maintained according to the method described by Taylor et al. (IRL Press, New York) and Galelli et al. (J. Immunol. (1990) 145:2397).

Inguinal ganglion cells (4 $10^6$/ml) from DBA/2 mice which 8 days before removal of the cells had received an injection at the base of the tail of 100 µg of KLH in emulsion in complete Freund's adjuvant were cultured for 4 days in the culture medium in the presence of KLH (100 µg/ml).

The cultures were incubated in a humid atmosphere under 7.5% of $CO_2$ at 37° C.

A cell line was established from this initial culture by serial passage of T cells purified on Ficoll ($2.10^5$/ml) in the presence of DBA/2 mouse spleen cells which had been irradiated (3000 rads) for 6 to 8 days (rest period) or with irradiated spleen cells plus KLH (100 µg/ml) for 4 days (stimulation period).

The T cells used in these experiments were collected 8 to 10 days after their last contact with KLH.

1.5 Estimation of the Th cell proliferation.

Cultures in triplicate containing $5.10^4$ Th cells purified on Ficoll, and $5.10^4$ purified and irradiated (900 rad) TNP-specific memory B cells, or $5.10^5$ irradiated (3000 rad) entire spleen cells, or $10^5$ irradiated (3300 rad) adherent spleen cells, or $10^5$ irradiated (3300 rad) A20 B cell lymphoma cells positive for class II MHC (Kim et al., J. Immunol. (1979) 122:549), or $10^5$ TNP-specific virgin B cells activated by LPS as source of the cells presenting the antigens, and different concentrations of antigen were incubated in flat-bottomed microculture plates (Corning, Cambridge, Mass.) under a total volume of 0.2 ml/well of complete medium. The T cell proliferation was estimated by incorporation of tritiated thymidine during the final eight hours of 3 days' culture.

The results are expressed as the geometric mean of three cultures, after elimination of background noise. The standard deviation was less than 15% of the mean.

1.6 TNP-Specific B cells.

The TNP-specific B cells from normal mice were purified by adsorption and elution on TNP8-gelatin according to the method described by Haas and Layton J. E., J. Exp. Med. (1975) 141:1004.

This method was modified in order to obtain populations enriched in TNP-specific memory B cells from spleens from previously immunized mice, as described previously (Galelli et al., J. Immunol. (1990) 145:2397)). The TNP-specific memory B cells were selected on the gelatin carrying a hapten (TNP2-gelatin), by testing the affinity of TNP receptors by comparison with virgin B cells, and the capacity to secrete large quantities of anti-TNP immunoglobulin G in the presence of low antigen concentrations.

$10^8$ spleen cells containing neither erythrocytes nor dead cells were suspended in 3 ml of HEPES (50 mM) buffered with DMEM (Seromed, Munich, Germany) and incubated in plastic Petri dishes covered with TNP2-gelatin. The dishes were gently agitated for 15 minutes at 4° C., then washed 10 times with DMEM at ice temperature. The adherent cells were eluted by the addition of 5 ml of DMEM reheated to 37° C. and the bonded TNP-gelatin was eliminated by digestion with collagenase (CLSIII Collagenase from Worthington Biochemicals, Freehold, N.J., 100 U/ml) for 15 minutes at 37° C.

This method gives an overall yield, expressed as a percentage of the original number of spleen cells, of 0.3 to 0.6% of cells bonding to TNP from the immunized mouse spleen. The cells were cultured overnight, before the addition of other cells and reagents, in order to enable the reexpression of surface immunoglobulins modified by the treatment with the collagenase. The presence of free TNP receptors on the cells was evaluated from their capacity to bind erythrocytes carrying TNP on their surface.

55 to 76% of the cells obtained from the immunized mice formed rosettes with the mouse spleen B cells modified by the TNP. These cells did not proliferate in response to concanavalin A but were 20 times enriched, for the cells which secreted anti-TNP immunoglobulin G after stimulation by TNP-LH, by comparison with non-fractionated spleen cells.

1.7 TNP-Specific virgin B cells activated by LPS.

TNP-Specific virgin B cells from non-immunized mice were purified by adsorption and elution on TNP8 gelatine as described previously. These cells were cultured to a density of $2.10^6$ per ml in a medium containing 50 µg/ml of LPS (Salmonella enteriditis, Difco Laboratories, Detroit, Mich.) for 3 days. The non-adherent lymphoblasts were purified by use of Ficolle-Hypaque (Pharmacia, Piscataway, N.J.), then washed and used as secondary cells.

1.8 Macrophages.

The macrophages were obtained from non-immunized spleen cells by adhesion for 4 hours at 37° C. followed by washing of the cells in order to eliminate the non-adherent cells as previously described (Kakiochi et al., J. Immunol. (1983) 131:109).

2. Results.

2.1 Verification of antigen coupling to the microparticles.

The KLH was covalently bonded to polyacrolein microparticles with diameter between 0.25 and 1.5 µm. The coupling of the KLH to the microparticles was checked by flow cytofluorimetric analysis using anti-KLH mouse serum.

The results obtained with 1.5 µm microparticles are shown in FIG. 1.

The 1.5 µm microparticles were coupled to ovalbumin (B OVA) or KLH (B-KLH). The TNP-OVA or TNP-KLH microparticles (designated respectively B(TNP-OVA) and B(TNP-KLH)) were prepared by incubation of microparticles carrying OVA or KLH with TNBS. The cytofluorimetric analysis was carried out on microparticles incubated in the presence of PBS or anti-KLH or anti-TNP mouse serum. After washing, the microparticles were incubated with goat antibodies bonded to FITC directed against mouse immunoglobulins and were analyzed by flow cytometry.

Similar results were obtained with 0.25 and 0.75 µm microparticles.

Control microparticles coupled to ovalbumin were not recognized by the anti-KLH serum.

2.2 Comparison of the ability of different splenocyte populations to present soluble or particulate antigens.

The ability of non-fractionated splenocytes, macrophages, and TNP-specific virgin B cells was compared for presentation of soluble or particulate KLH and TNP-KLH to KLH-specific T cells.

In these experiments the splenocyte populations were prepared from non-immunized mice. After purification, the TNP-specific B cells were activated for three days by LPS; it is known that the lymphoblasts induced by LPS are extremely efficient for antigen presentation (Kakiochi et al., J. Immunol. (1983) 131:109).

The results are illustrated in FIG. 2 for which $5.10^8$ irradiated splenocytes, $10^5$ adherent cells or $10^5$ TNP-specific virgin B cells activated by LPS were cultured with $5.10^4$ KLH-specific Th cells in the presence of different quantities of soluble KLH (A), soluble TNP-KLH (B), or fixed on microparticles (B KLH) (C), or (B TNP-KLH) (D). The Th cell proliferation was estimated on day 3.

As shown in FIG. 2 (2A and 2B) the macrophages and the B cells activated by LPS efficiently stimulated the T cells when they were incubated with soluble KLH or TNP-LH.

In contrast to these results, only the macrophages, and not the LPS-activated TNP-specific B cells, were able to stimulate the KLH-specific T cells (FIGS. 2C and D) when the microparticles carrying KLH or TNP-KLH were used.

These results show that the macrophages are responsible for the activity of spleen cell antigen presentation when particulate antigens are used.

The inability of the TNP-specific B cells to present the particulate antigen has thus been demonstrated.

EXAMPLE 2

Induction of a lysozyme specific CD4+ T-proliferative response in vivo and in vitro by lysozyme-coupled microparticles.

1. MATERIALS AND METHODS.

1.1 Antigens.

The lysozyme (LYSO) and the Limulus hemocyanin (LH) were from Sigma Laboratories.

1.2 Coupling of the antigen to the microparticles.

The soluble antigen was made particulate by coupling to microparticles (Polysciences) of between 0.2 and 1 µm diameter. Two coupling methods were used:

1.2 a) Direct covalent coupling without activating agent.

The polyacrolein beads or microparticles possess aldehyde groups capable of spontaneous reaction with the amine functions of the proteins.

1 ml of beads were washed 4 times in PBS and then taken up in 1 ml of antigen at 5 mg/ml concentration. After 3 hours' incubation at ambient temperature, the beads were washed 3 times in PBS and incubated for 30 minutes in 1 ml of PBS-1% human albumin in order to saturate the free reactive groups on the beads. After washing, the particles were then taken up in 2 ml of PBS-1% human albumin-1% antibiotic and stored at +4° C.

b) Covalent coupling by glutaraldehyde.

The antigen was coupled to polystyrene beads by glutaraldehyde, which was capable of forming a Schiff's base with the protein amine groups.

0.5 ml of beads were washed 3 times in PBS and taken up in 0.5 ml of 8% glutaraldehyde. After 6 hours' incubation at ambient temperature, the beads were washed twice and then taken up in 1 ml of antigen at concentration 400 µg/ml. After incubation overnight at ambient temperature, the beads were washed and incubated with 1 ml of 0.2 M ethanolamine for 30 minutes in order to block the free aldehyde functions of the glutaraldehyde.

After a final washing, the particles were taken up in 1 ml of PBS-1% human albumin-1% antibiotic then stored at +4° C.

This coupling method enabled the quantity of proteins coupled to the microparticles to be determined by spectrophotometry. The absorbances of the 400 µg/ml protein solution and the supernatant obtained after incubation of the beads with this protein solution were measured at 280 nm. Given the number of beads used for the coupling, the difference between the quantity of protein before coupling and the residual quantity after coupling could be used to estimate the quantity of lysozyme coupled per particle.

1.3 Immunization protocol.

BALB/c females, haplotype $h-2^d$, aged 6 to 9 weeks (reared in the Institut Pasteur) were used.

immunization by intra-peritoneal route: 100 µg of lysozyme with 1 mg of alum were injected, or different quantities of antigen coupled to beads without adjuvant, immunization by subcutaneous route: 100 µg of lysozyme in emulsion with complete Freund's adjuvant were injected at the base of the tail, or different quantities of antigen coupled to beads.

The serum of each mouse was sampled 7 to 14 days after injection. The antibody strength of the serum was measured by the ELISA assay.

The cell proliferative response was measured on inguinal ganglions and/or on the spleen, sampled 7 and/or 14 days after each injection.

1.4 Detection of antibodies by ELISA.

The antigen (lysozyme) was incubated at a concentration of 5 µg/ml in 50 mM pH 9.6 carbonate buffer in the microplates (Nunc) for one night at 4° C. After washing with a 0.01% PBS-Tween 20 buffer, the different serum dilutions to be tested, in 1% BSA buffer, were incubated for 1 hour at 37° C. After washing, 100 µl of a mouse anti-Ig conjugate (complete anti-Ig supplied by Diagnostics Pasteur and specific anti-Ig by Sigma) were placed in each well, marked with goat peroxidase; this was incubated for 1 hour at 37° C. After washing, a substrate solution was added freshly prepared as follows: 0.5 mg/ml of orthophenylenediamine (Sigma) in a 0.1M citric acid-0.2M disodium phosphate buffer, pH 5, to which was added $H_2O_2$ to 1/2500.

A yellow coloration revealed the presence of specific antibodies; the enzyme reaction was stopped 8 minutes later by the addition of 50 µl of 11.5% $H_2SO_4$.

The absorbance of each well was measured at 492 nm by an optical density reader (Dynatech). The negative control was made with 1:100 serum from non-immunized BALB/c mice. The results are expressed either in ODx1000 from measured absorbance, corrected for the absorbance in absence of serum, or by the antibody titer calculated from the linear regression based on the absorbance obtained with the serum from the non-immunized BALB/c mice.

When the antigen was in particulate form, the ELISA assay was carried out in tubes. The serum dilutions to be tested were incubated directly with the antigen coupled to the beads ($8.10^8$ particles/ml). Washings were made by centrifuging in 0.1% PBS-Tween 20 buffer. When the enzyme reaction had finished, 200 µl from each tube was transferred onto a microplate and the absorbance then measured.

1.5 Inhibition of the fixation of the anti-lysozyme antibody by the ELISA assay.

The ELISA assay measured the fixation of specific antibodies present in the serum of the immunized BALB/c mice by the lysozyme. This fixation was reduced if the serum was preincubated (before the ELISA assay) with the antigen: soluble lysozyme or lysozyme coupled to beads, which then behaved as an inhibitor.

The anti-lysozyme serum was preincubated with soluble lysozyme or lysozyme coupled to beads for 1 hour at 37° C., then for 1 night at 4° C.; the reaction was carried out in the tubes. The fixation of antibodies not bonded to the inhibitor was evaluated by the ELISA assay (triplicates) on microplates, in which the wells were covered with 5 µg/ml of lysozyme. The absorbance of each well was measured at 492 nm, and corrected for the absorbance in the absence of serum. The negative control was carried out with 1:100 serum from non-immunized BALB/c mice. The absorbance without inhibitor during the preincubation of the serum corresponded to the maximum anti-lysozyme antibody fixation.

Results are expressed as a percentage of the inhibition of the antibody fixation and calculated according to the ratio $$\frac{\text{OD without inhibitor} - \text{OD with inhibitor}}{\text{OD without inhibitor}}$$

The graphical representation of the soluble lysozyme concentration necessary for 50% inhibition, together with the number of beads coupled to lysozyme, enabled estimation of the quantity of lysozyme fixed per particle.

1.6 Stimulation of a lysozyme-specific T hybridoma

A T hybridoma was produced by immunization of BALB/c mice with lysozyme. It specifically recognized peptide 108–116 of lysozyme, in combination with molecules of the class II I-$E^d$ Major Histocompatibility Complex.

$10^5$ T hybridoma cells were stimulated by increasing antigen concentrations: lysozyme or coupled beads, in the presence of different cells presenting the antigen: $5.10^5$ irradiated splenocytes (3000 rad) of BALB/c mice or $10^5$ cells of B lymphoma A20, restricted by Class II MHC molecules. The cells were cultured (in triplicate) in a complete RPMI medium (SEROMED) supplemented with 10% decomplemented fetal calf serum, 50 µM β-mercaptoethanol, 2 mM glutamine, 100 UI/ml penicillin and 100 µg/ml streptomycin, on flat-bottomed microplates (Corning 25860). The positive control was performed by stimulation of the hybridoma by the T lymphocyte mitogen:concanavalin A at 5 µg/ml.

The supernatant was removed after 24 h culture at 37° C. (7.5% $CO_2$), then frozen to −20° C. for a minimum of 16 h. The stimulation of the hybridoma was measured by the IL2 concentration of the supernatant in a CTL-L cell proliferation test. Standard deviations have not been given as the error was lower than 10% of the mean of the triplicates.

1.7 Determination of IL2 and IL4

The CTL-L line is dependent on Interleukin 2 and Interleukin 4; it was maintained in culture in complete medium enriched with 20% of rat splenocyte supernatant, incubated 36 h with 2.5 µg/ml of concanavalin A.

After thawing, the culture supernatants (tested 1/2) were incubated in the presence of $2.25.10^4$ CTL-L cells, previously washed three times in RPMI 1640 medium, for 3 days at 37° C. (7.5% $CO_2$).

The cell proliferation was measured by the addition of tritiated thymidine with specific activity 1 Ci/mmole, at a level of 2 µCi/ml of culture, for the last 16 hours of culture.

The cell DNA was recovered after cell lysis and filtration using a "Skatron". Radioactivity incorporation was counted by scintillation using a beta counter.

The results are expressed in cpm based on the mean of the triplicates, corrected for the radioactivity incorporated in the absence of antigen.

1.8 Proliferation test

The spleen and/or the inguinal ganglions were removed under sterile conditions 7 or 14 days after immunization of the mice (see immunization protocol). $8.10^5$ Cells were incubated in the presence of different concentrations of antigen, soluble or coupled to beads. The cells were cultured (in triplicate) in RPMI 1640 medium (SEROMED) supplemented with 1.5% decomplemented fetal calf serum, 0.5% normal mouse serum, 50 µM β-mercaptoethanol, 2 mM glutamine, 100 UI/ml penicillin and 100 µg/ml streptomycin, on microplates (Corning 25860) for 4 days at 37° C. (7.5% $CO_2$).

The cell proliferation was measured by the incorporation of tritiated thymidine with specific activity 25 Ci/mmole, at a level of 2 µCi/ml of culture, for the last 16 hours of culture. The cell DNA was recovered after cell lysis and filtration using a Skatron. Radioactivity incorporation was counted by scintillation using a beta counter.

The results are expressed in cpm based on the mean of the triplicates, corrected for the radioactivity incorporated in the absence of antigen.

2—RESULTS.

2.1. Stimulation of ganglion cells from mice immunized with lysozyme by lysozyme coupled to microparticles.

Figure 3A:
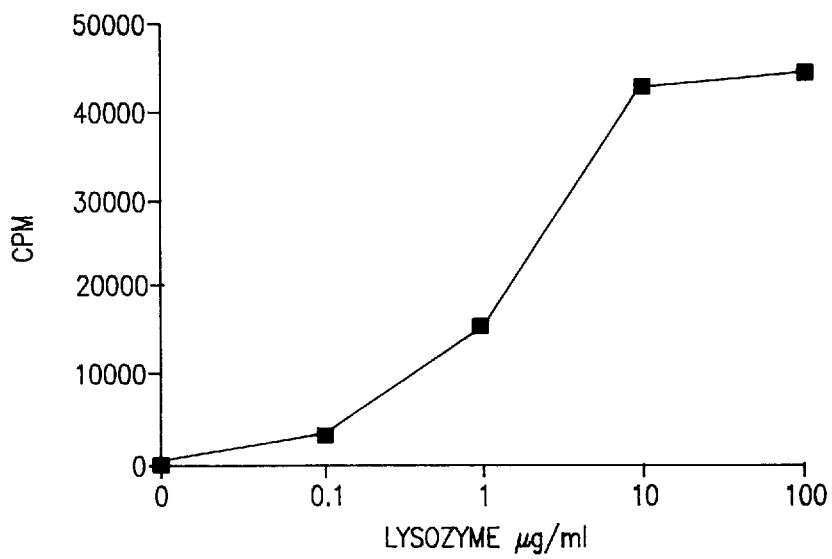
Figure 3B:
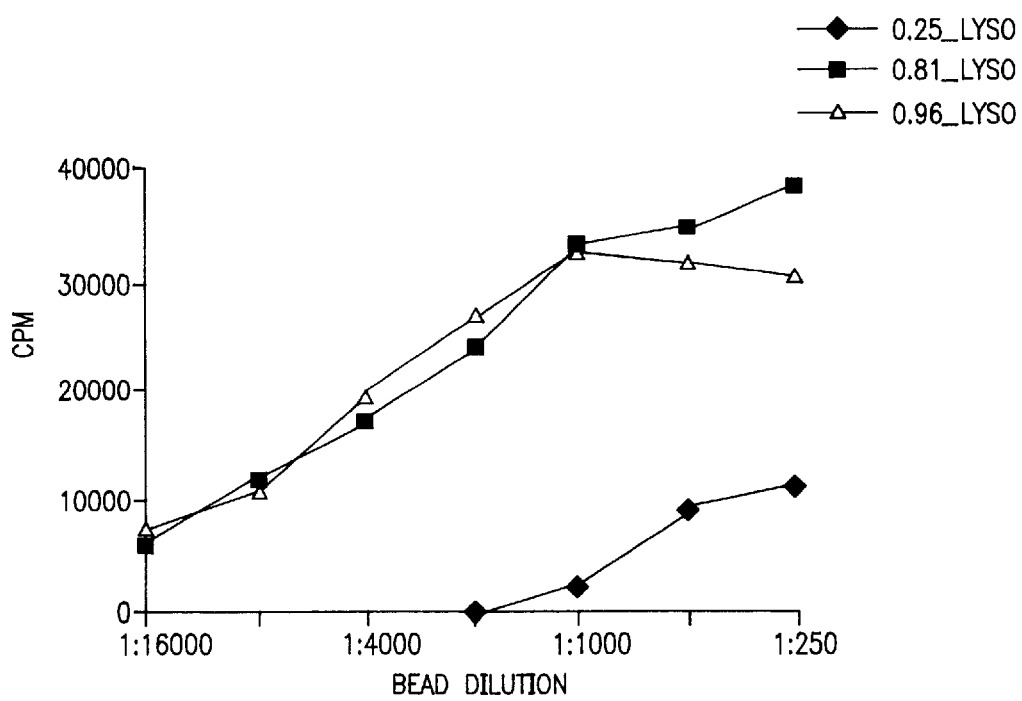

In the tests illustrated by FIGS. 3A and 3B, BALB/c mice were immunized by subcutaneous injection at the base of the tail of soluble lysozyme complemented with Freund's adjuvant (CFA).

After 14 days, the inguinal ganglions were removed, and the proliferative response of these cells was tested in vitro against different concentrations of lysozyme or against different concentrations of microparticles coupled to lysozyme. The results are expressed in cpm corrected for the value obtained without antigen.

Soluble lysozyme induced substantial proliferation of cells from mice immunized by this antigen in Freund's adjuvant (3A). The in vitro stimulation of these cells by lysozyme-microparticles revealed that the latter are able to induce a very strong cell proliferation (FIG. 3B). The microparticles with very large diameter, 0.81 and 0.96 $\mu$m (spontaneous coupling), were very effective.

2.2. Stimulation of T hybridoma by lysozyme coupled to beads

Figure 4A:
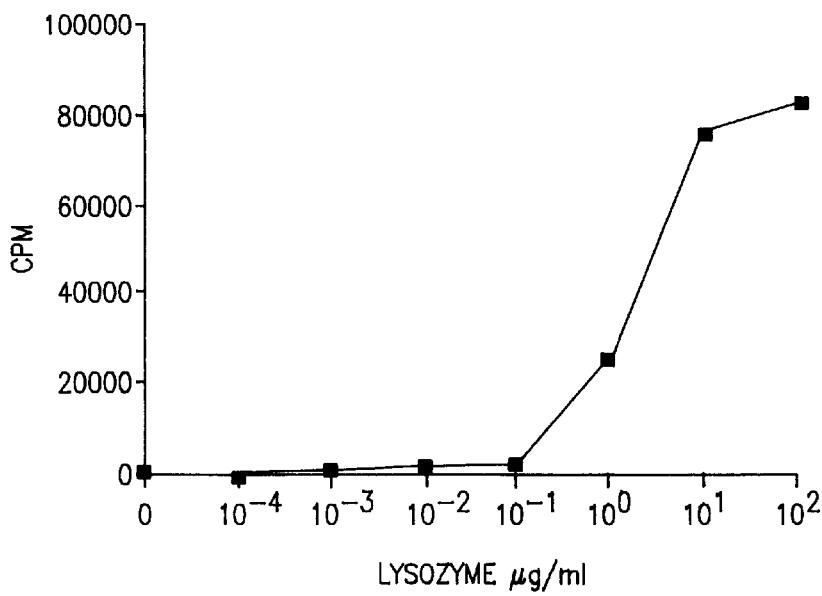
Figure 4B:
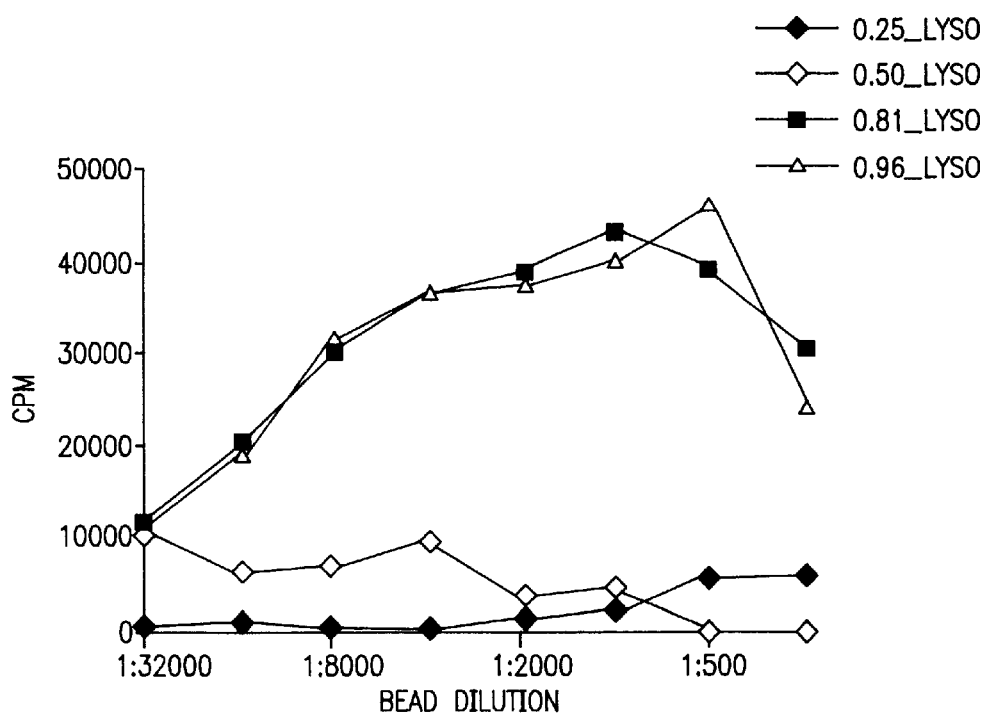

FIGS. 4A and 4B correspond to the results for stimulation of lysozyme-specific T hybridoma by soluble lysozyme (4A) or lysozyme coupled to microparticles (4B). The degree of stimulation of the hybridoma was measured by the level of IL-2/IL-4 produced.

In the presence of irradiated splenocytes, the T hybridoma was strongly stimulated by soluble lysozyme (FIG. 4A). In the presence of these cells, the large lysozyme-microparticles (0.81 and 0.96 $\mu$m) also caused substantial production of IL-2/IL-4 (FIG. 4B), in contrast to the 0.5 and 0.25 $\mu$m microparticles which were not able to stimulate the specific T hybridoma.

2.3. Inability of B lymphoma A20 cells to present lysozyme coupled to beads to lysozyme-specific T hybridoma.

It is known that B cell tumors carrying Ia receptors can be used as antigen-presenting cells for antigens which do not react with the Ig receptor but which are fixed by B cell tumors by nonspecific mechanisms (Walker et al., J. Immunol. (1982) 128:2164; Glimcher et al. J. Exp. Med (1981) 155:445; MacKean et al. J. Exp. Med. (1981) 154:1419).

The capacity of one of these B cell tumors, the A20 line, to present lysozyme in soluble or particulate form was thus tested.

Figure 5A:
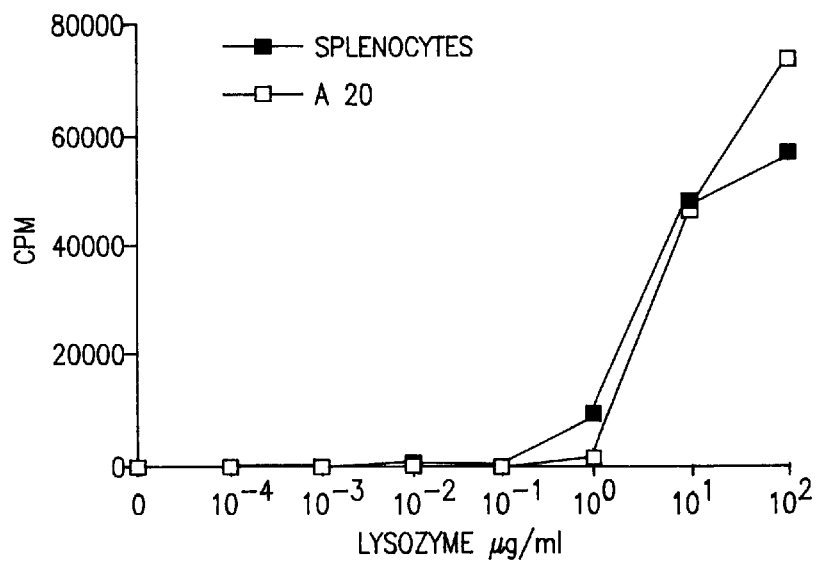
Figure 5B:
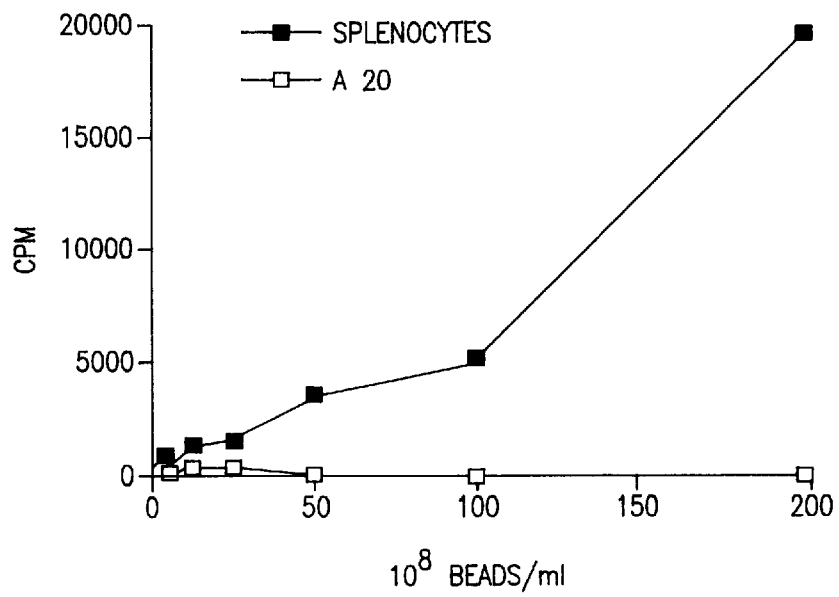

The presentation of soluble or particulate lysozyme was compared using two sources of antigen-presenting cells: either a heterogenous source, irradiated entire splenocytes, or B cells from the A20 lymphoma. When the antigen was in soluble form (FIG. 5A), it could stimulate the T hybridoma equally well in the presence of splenocytes as of A20 B cells. However, particulate lysozyme was presented only by splenocytes and not by A20 B cells (FIG. 5B).

These results confirm that splenocytes can present an antigen to T cells, either in soluble or particulate form. However, B lymphocytes. were not able to present an antigen rendered particulate by coupling to a bead of a size of the order of a micron.

2.4 Induction of T proliferative responses by injection of lysozyme coupled to microparticles to mice.

The in vivo immunogenicity of the antigen coupled to microparticles was analyzed by immunizing BALB/c mice with lysozyme in complete Freund's adjuvant or with this antigen coupled to polyacrolein beads. After 14 days, cells from draining ganglions of these animals were stimulated in vitro by different concentrations of soluble lysozyme.

Figure 6A:
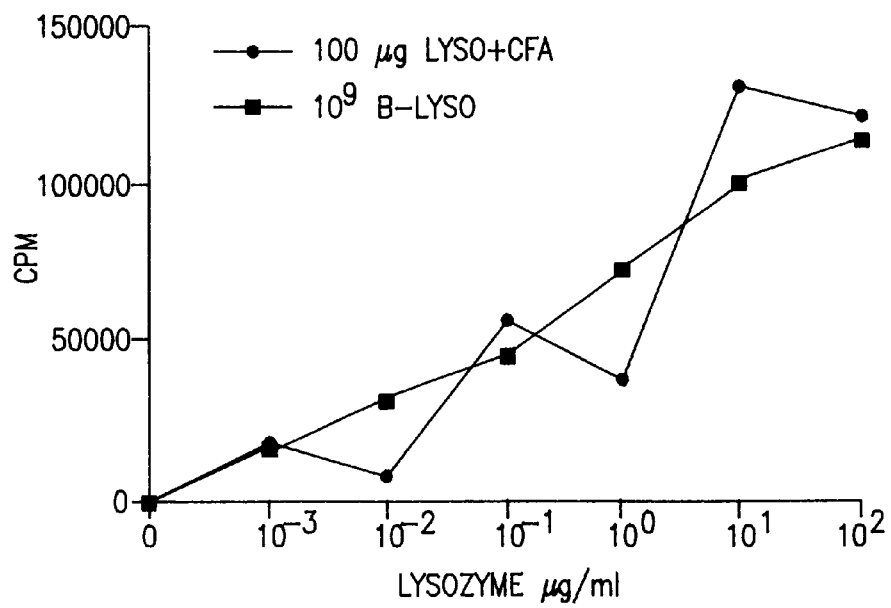
Figure 6B:
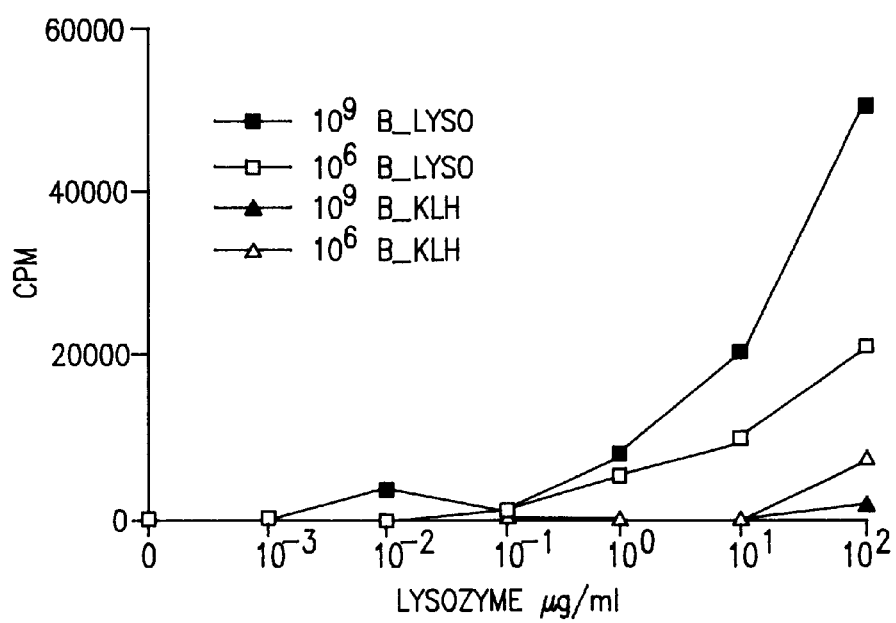

In the presence of soluble lysozyme, the ganglion cells proliferated strongly, whether originating from mice immunized with soluble lysozyme or lysozyme-microparticles (FIG. 6A). This shows that in both cases lysozyme-specific T cells were sensitized in vivo. After injection of LH-microparticles to mice, representing the specificity control, the ganglion cells of these animals were not able to proliferate in response to stimulation by soluble lysozyme in vitro (FIG. 6B). The cellular response in vivo is thus specific to the protein antigen coupled to microparticles, used during immunization of the mice.

The proliferative response of the cells sensitized by $10^9$ lysozyme-microparticles (corresponding to 1 $\mu$g of lysozyme), in the absence of adjuvant, was as high as that of cells from animals immunized with 100 $\mu$g of lysozyme in Freund's adjuvant (CFA) (FIG. 6A). In order to. confirm and clarify this result, proliferative responses of ganglion cells from animals having received different doses of lysozyme in CFA or different concentrations of coupled microparticles were compared, after in vitro stimulation by soluble lysozyme.

Figure 7A:
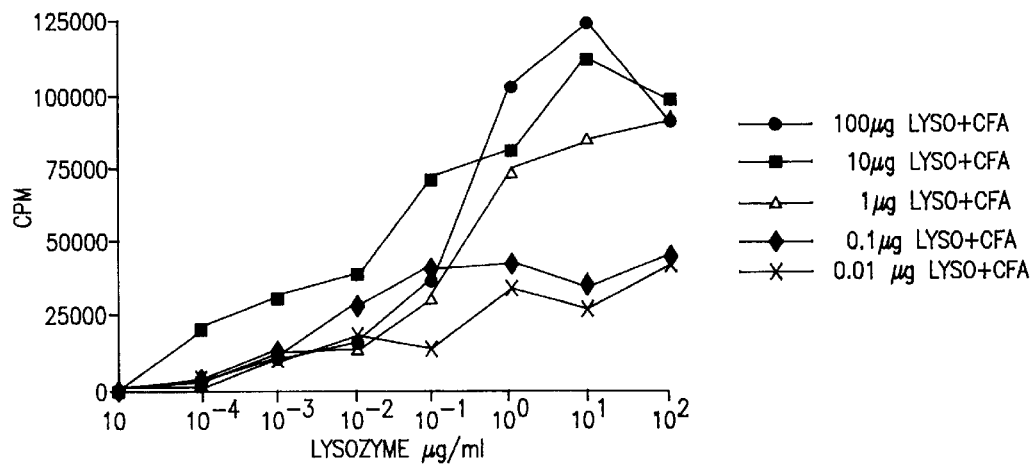
Figure 7B:
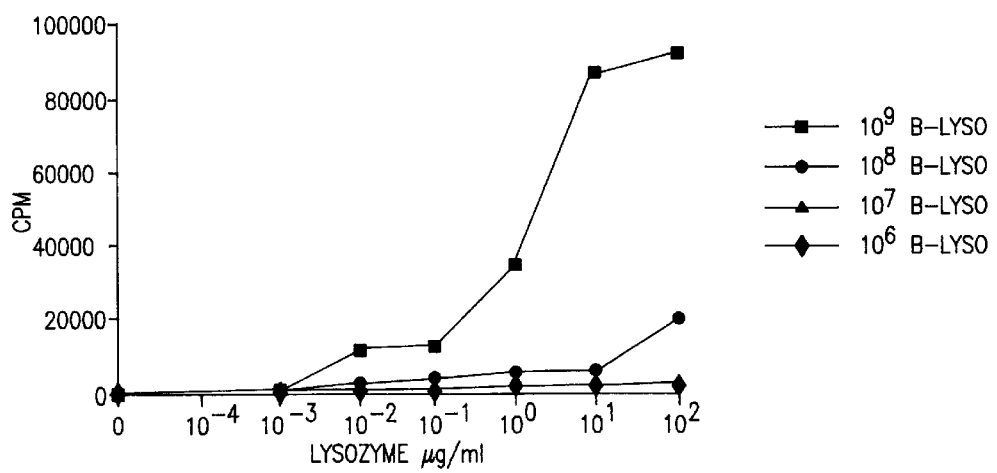

In the case of FIGS. 7A and 7B, the mice had been immunized by subcutaneous injection at the base of the tail of soluble lysozyme and complete Freund's adjuvant (CFA) (FIG. 7A) or beads coupled to antigen without adjuvant (FIG. 7B).

After 14 days, the inguinal ganglions were removed, and the proliferative response of these cells was tested in vitro against different lysozyme concentrations. The results are expressed in cpm corrected for the value obtained without antigen.

In FIG. 7B, it should be noted that the designations $10^9$, $10^8$, $10^7$ and $10^6$ B-LYSO correspond respectively to weights of 1; 0.1; 0.01 and 0.001 $\mu$g of lysozyme.

These results show that the ganglion cells from animals immunized with lysozyme-carrying microparticles proliferate in vitro after contact with lysozyme, thus demonstrating sensitization of the T cells specific for this antigen.

Comparison of the concentration effects (FIG. 7) shows that 1 $\mu$g of lysozyme coupled to beads gives a response quasi-equivalent to that of 1 $\mu$g of antigen injected in CFA.

Figure 8:
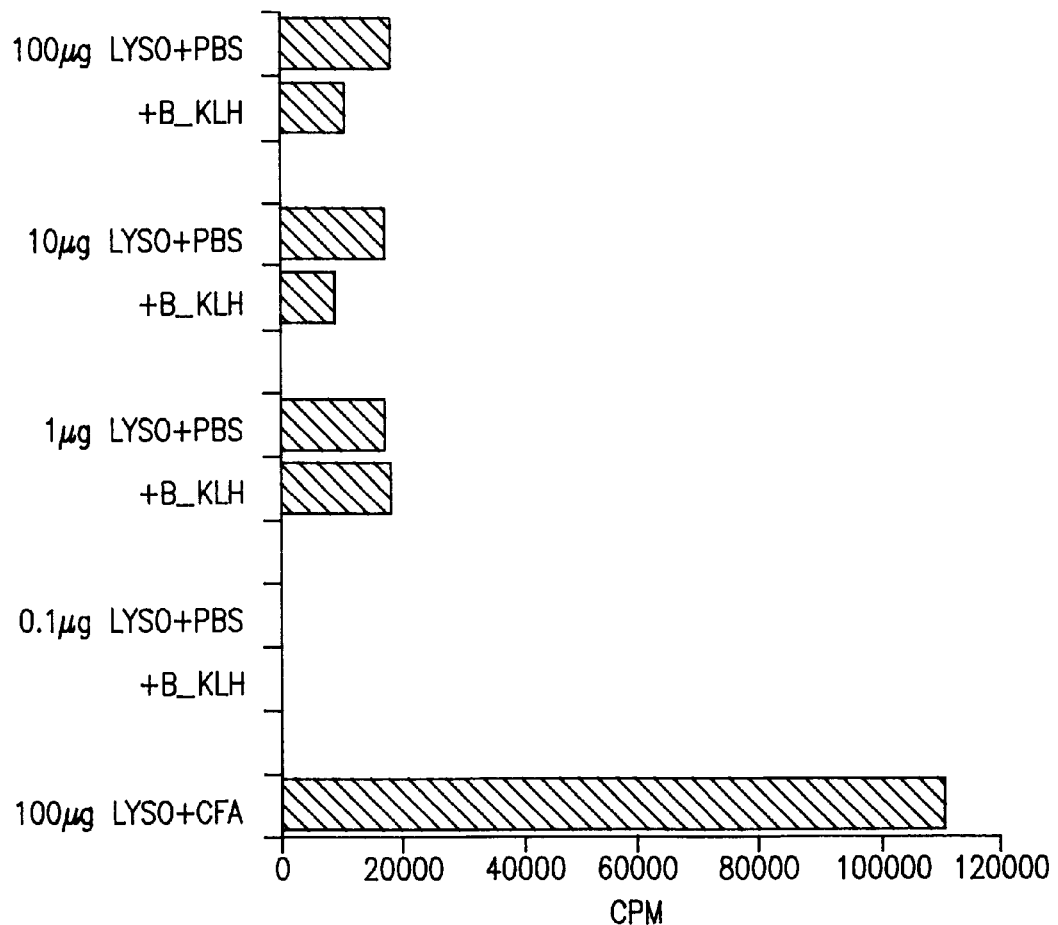

FIG. 8 represents the proliferative response of cells from mice immunized with lysozyme in complete Freund's adjuvant (CFA) or in PBS with microparticles coupled to LH. The addition of LH beads to lysozyme did not lead to induction of high proliferative responses, which shows that the lysozyme must be covalently coupled to the microparticles to induce T-proliferative responses.

2.5—Induction of T-proliferative responses by injection of mice with hemoglobin or ovalbumin coupled to microparticles Mice were immunized with hemoglobin or ovalbumin in complete Freund's adjuvant, or with these proteins covalently coupled to the same type of particles as in the previous examples (polystyrene, 1 $\mu$m diameter).

The ganglion cells from these animals were restimulated in vitro by the soluble proteins and the cell proliferation was measured.

Figure 9:
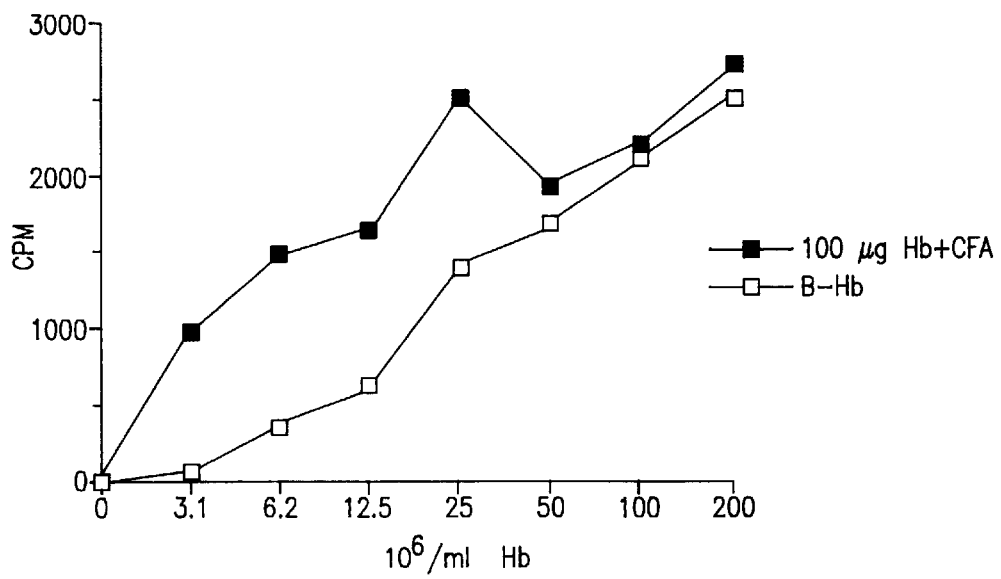
Figure 10:
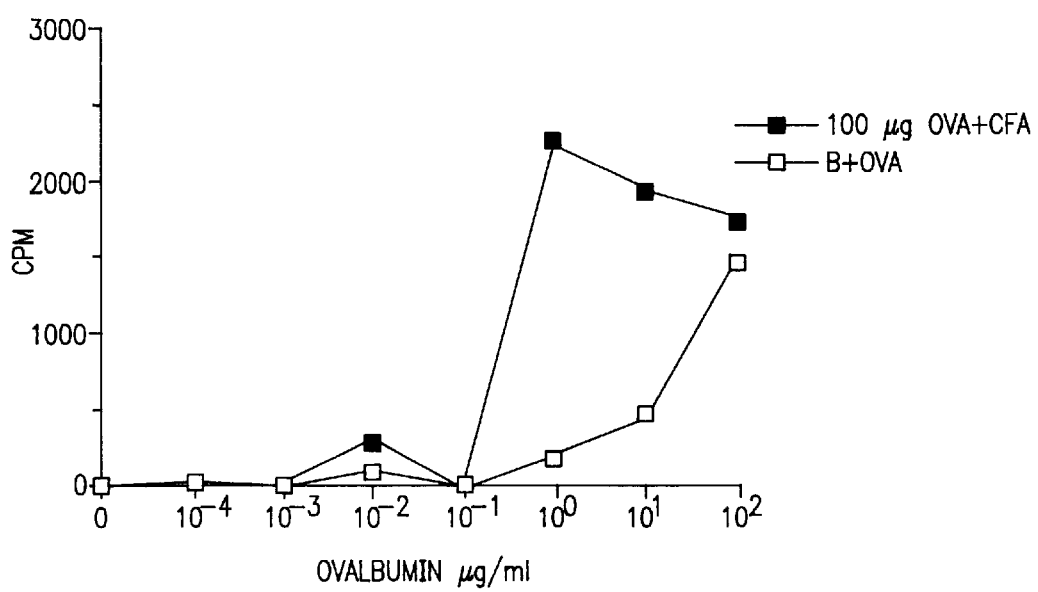
Figure 11:
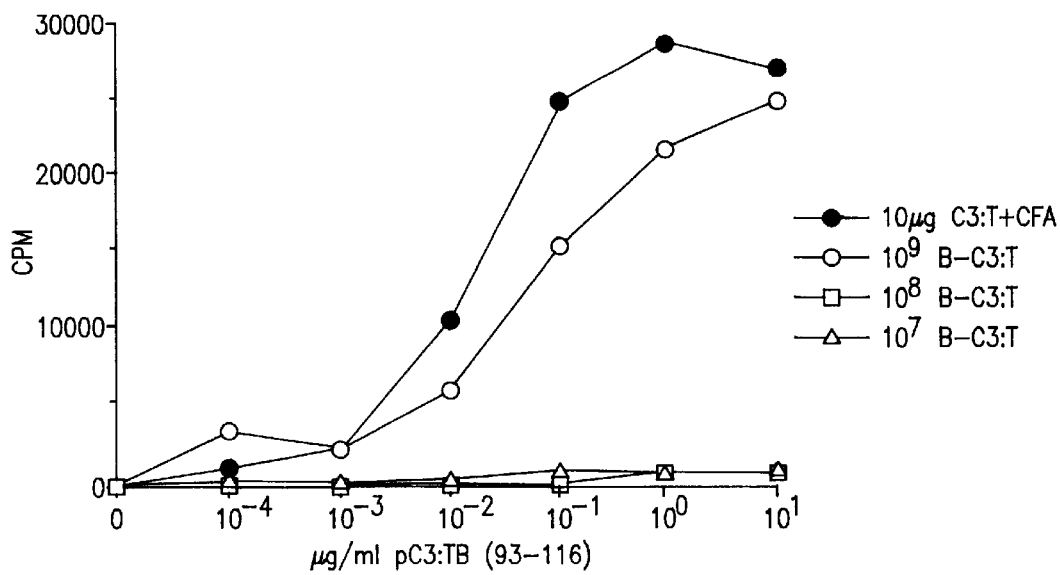
Figure 12:
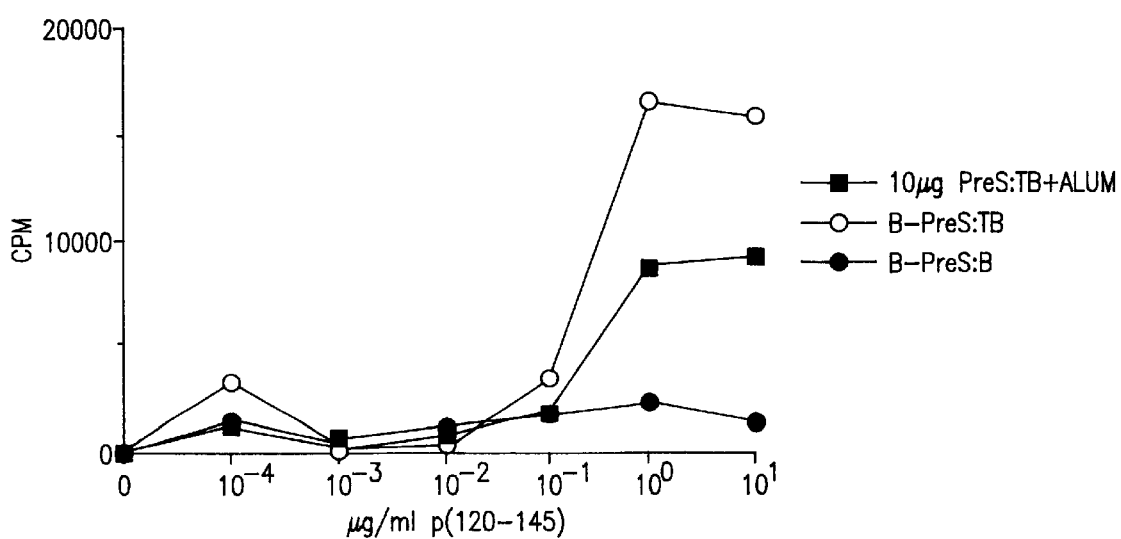
Figure 13A:
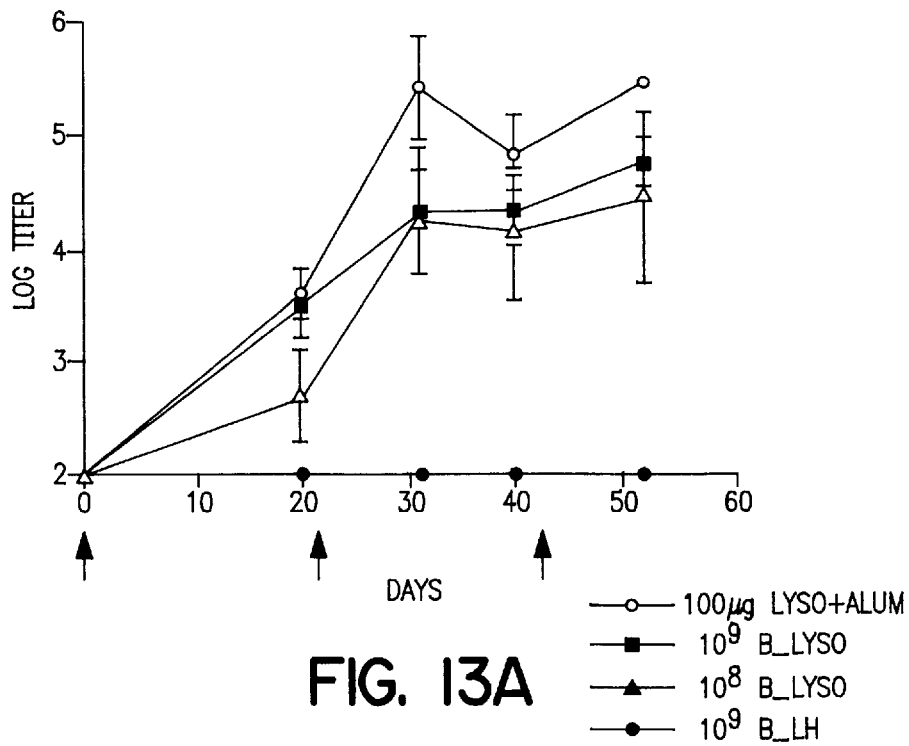
Figure 13B:
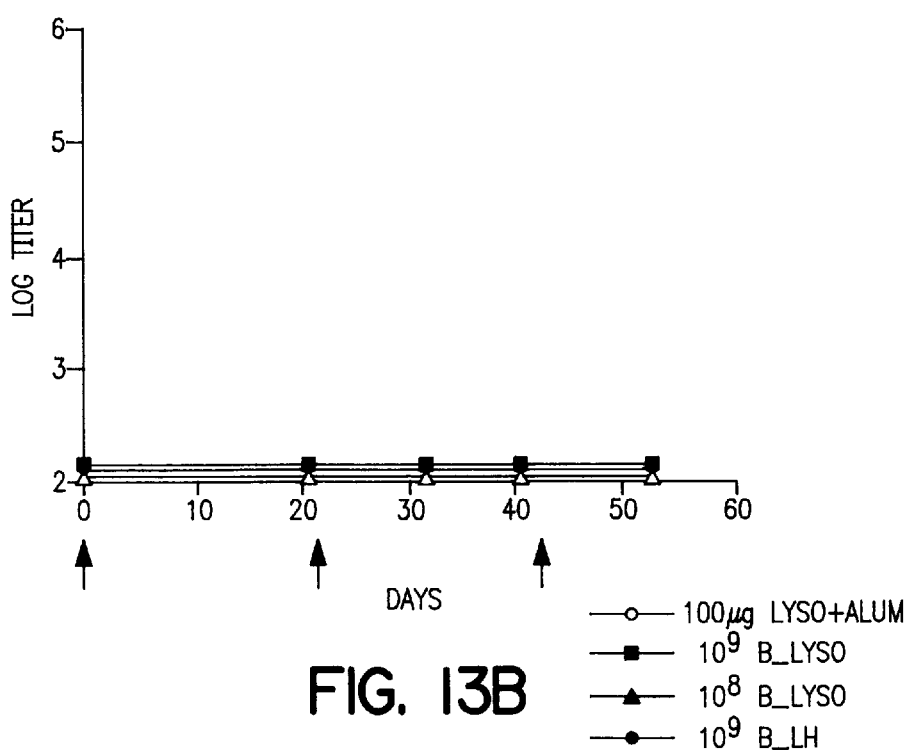
Figure 14:
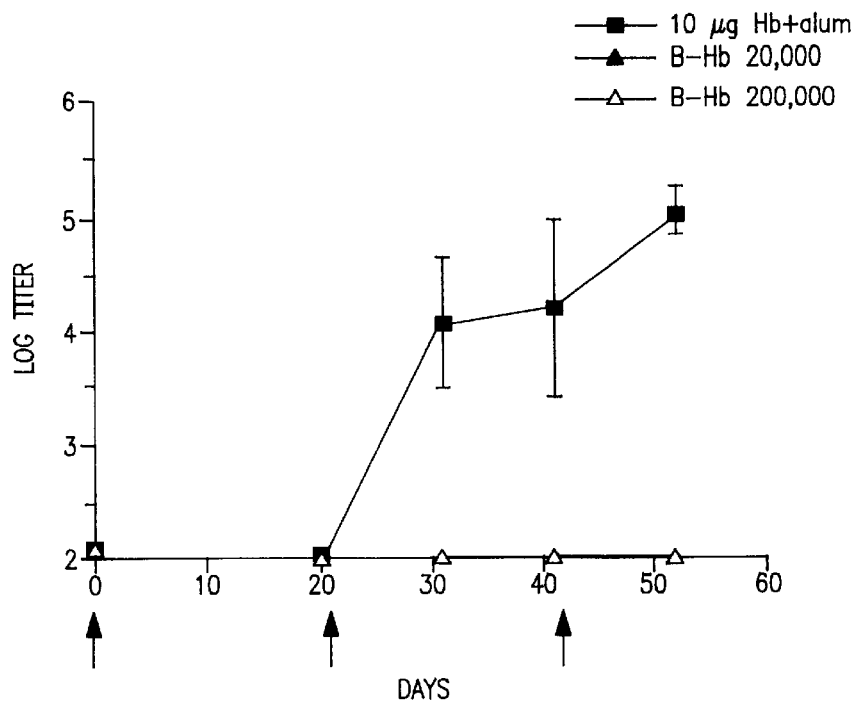
Figure 15:
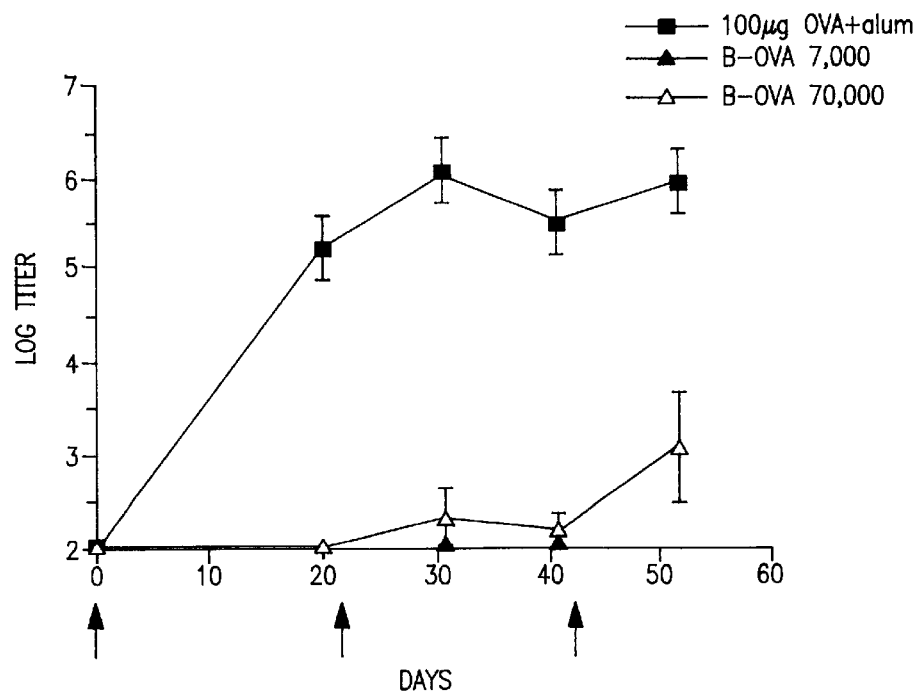
Figure 16:
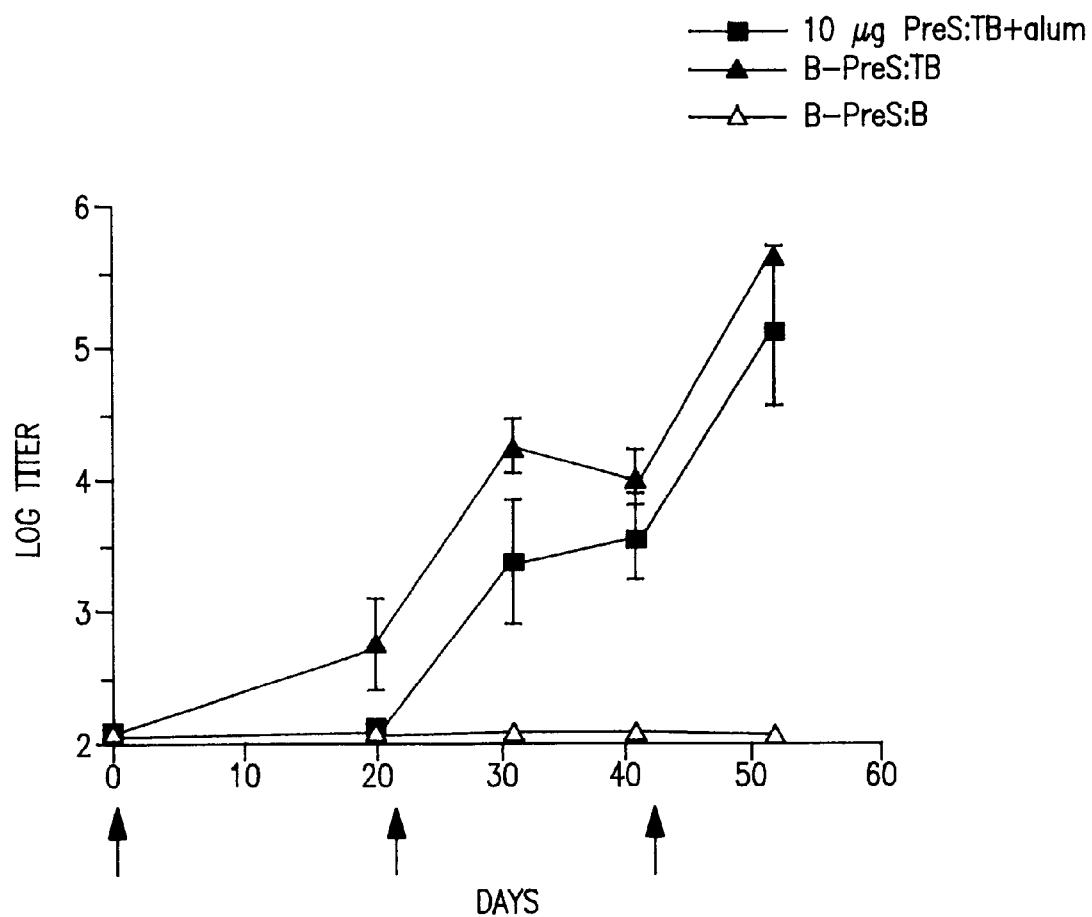

The results obtained for hemoglobin (Hb) are shown in FIG. 9, while FIG. 10 shows the results obtained for ovalbumin (OVA).

These results overall show that these proteins coupled to microparticles are able to sensitize CD4+ T lymphocytes specific to these proteins in vivo, in the absence of adjuvant.

2.6—Induction of T-proliferative responses by injection of synthetic peptides 2.6.1—T Epitope from region C3 of the VP1 protein The T epitope of the C3 region (C3: T, 103–115) of the poliovirus protein was synthesized and covalently coupled to 1 μm beads. These beads were injected into BALB/C mice.

The results in FIG. 11 clearly show that the T epitope coupled to the beads (B-c3:T) induced a strong T-proliferative response for quantities of the order of $10^9$ beads injected per mouse.

2.6.2—Pre-S:T peptide of the HBS antigen

The pre-S:T peptide (120–132) of the HBS antigen was synthesized and covalently coupled by glutaraldehyde to beads of 1 μm diameter.

FIG. 12 shows that the injection of $10^9$ beads to DBA/1 mice induced a strong T-proliferative response, stronger than that obtained with the peptide in CFA. The injection of beads not containing the B epitope did not induce a proliferative response, showing the specificity of the response.

EXAMPLE 3

Induction of antibody response by microparticles carrying an antigen.

The materials and methods were similar to those of Example 2.

1. Lysozyme or Limulus hemocyanin

For FIGS. 13A and 13B, BALB/c mice were immunized by intra-peritoneal injection with 100 μg of soluble lysozyme in adjuvant (alum) or with beads coupled to antigen:lysozyme or Limulus hemocyanin (LH), without adjuvant.

The injections-were carried out at D0, D21, D42, the serums were taken at D20, D31, D40 and D52 and assayed by ELISA for their antibody content. The results are expressed in log10 of the titer of anti-lysozyme antibody. (FIG. 13A) and anti-KLH antibody (FIG. 133).

Three antigen injections were performed i.p. at days 0, 21 and 42. The lysozyme-microparticles gave very good antibody responses while no antibody response was induced by the LH microparticles. These microparticles moreover very efficiently stimulated T responses.

One of the differences between LH and lysozyme is their molecular weights (14500 for lysozyme and 71000 for LH).

2. Hemoglobin and ovalbumin

Mice were immunized with soluble antigen in alum adjuvant or with the same antigen in particulate form, in the absence of adjuvant. Antibody appearance was then monitored over several weeks.

In the case of hemoglobin (Hb), the mice were immunized with 100 μg of protein or $10^9$ beads coupled with the protein at different densities ($2.10^4$ and $2.10^5$ molecules $\mu m^2$). The beads carrying ovalbumin (OVA) were tested at two densities, $7.10^3$ and $7.10^4$ molecules/$\mu m^2$.

An initial injection was carried out, followed by two more injections on the 21st and 40th days. Serums were taken at the 20th day, the 31st day, the 41st day and the 52nd day, then assayed by ELISA for their IgG antibody levels. The results are expressed in log of the antibody titer.

The results in FIG. 14 show that hemoglobin coupled to beads did not induce an antibody response. For ovalbumin (FIG. 15) antibodies were detectable after several injections if the antigen was coupled at high density, but these responses were weak. These results show that proteins of high molecular weight such as hemoglobin are not able to induce an antibody response, even if they are coupled at a high density on the beads.

These results, similar to those obtained with lysozyme and limulus hemocyanin, confirm that beads carrying high-molecular weight proteins induce T-proliferative responses in the absence of any antibody production.

3. Synthetic peptides.

The peptides pre-S:TB (120–145) and pre-S:B corresponding to the portions of the HBS antigen containing respectively a T epitope and a B epitope or only the B epitope were covalently coupled to 1 μm beads with glutaraldehyde (B-pre-S:TB and B-pre-S:B).

The antibody response induced by these beads was compared with that induced by 10 μg of soluble pre-S:TB peptide in alum adjuvant.

The results in FIG. 16 show that the beads coupled to the TB peptide, containing a T epitope and a B epitope, induced strong antibody responses, which confirms that antigens of low molecular weight coupled to beads are able to induce an antibody reaction in the absence of adjuvant. It may be noted that these responses are as good as those obtained with the free peptide in the presence of alum adjuvant.

EXAMPLE 4

Effect of the molecular weight of the protein bonded to the surface of the microparticles on antibody production.

1.1 Antigens and reagents.

Hen egg lysozyme (HEL) Limulus hemocyanin (LH) and ovalbumin were purchased from Sigma (St Louis, Mo.), β-galactosidase was obtained from Boehringer (Mannheim, Germany) and MalE protein was kindly given by DR. Martineau (Pasteur Institut, Paris, France). Peptides 93–103 (C3:B), 93–116 (C3:BT) from VP1 envelope protein of poliovirus type 1 and peptide 132–145 (Pres:B), 120–145 (PreS:TB) from HssAg of hepatitis B virus (HBV) were synthesized by Neosystem (Strasbourg, France).

Particulate forms of antigens were prepared by covalent linkage of proteins or peptides to lam-diameter latex particles (Polysciences, Warrington, Pa.) using glutaraldehyde (Sigma), as described in example 2. After incubation with gluirataldehyde, the particles were incubated with 400 μg/ml protein solution or 1 mg/ml peptide solution, and unreacted amino groups were then blocked with ethanolamine (Sigma).

HM40-3, a hamster anti-mouse CD40 monoclonal antibody was purchased from Pharmingen (San Diego, Calif.). 1.9, a hamster anti-clonotype γδmonoclonal antibody kindly given by Pablo Pereira (Pasteur Institute, Paris) was used as a control.

1.2 Immunization of mice and in vivo depletion of $CD4^{\pm}$

BALB/c female mice were purchased from Iffa Credo (L'Arbresle, France) and DBA/1 female mice were obtained from the breeding facilities of the Pasteur Institute (Paris, France). Mice of 8–10 weeks old, four or five per group, were i.p. injected with soluble antigen in adjuvant(1 mg of alum or CFA emulsion),or with particulate antigen without any adjuvant. For in vivo depletion of $CD4^+$ T cells, mice were i.p. injected with 300 μg of GK1.5 anti-CD4 mAb (Dialynas et al., 1984, J. Immunol., 131,2445), on days −1,0,+1 and once a week throughout the immunization period, to selectively eliminate $CD4^+$ T cells, as previously described (Leclerc et al., 1990, J. Immunol, 145, 1343; Fayolle et al., 1991, J. Immunol., 147, 4069).

1.3 In vitro antibody production assay

DBA/1 mice were injected i.p. on days 0 and 21 with 10 μg of PreS:TB peptide and 1 mg of alum. Four weeks after the last injection, spleens were surgically removed and cell suspensions were prepared in RPMI 1640 medium (Seromed, Munchen, Germany) containing 10% heat-inactivated FCS, 2 mM glutamine (Seromed), 2-mercaptoethanol and antibiotics (Seromed). $3\times10^6$ splenocytes were incubated with soluble or particulate peptides in a 800 μl final volume in 24 well microplates (Costar, Cambridge, Mass.). Control wells received no antigen. On the third day of culture, the plates were washed to remove the antigen and fresh medium was added to each well. Three days later, the culture supernatants were collected and tested by ELISA for the presence of peptide specific IgG antibodies. In some experiments, various doses of an anti-CD40 mAb or of the control mAb were added to the cultures at days 0 and 3.

1.4 Detection of antigen specific antibodies

Mice were bled at different times and sera from individual mice were tested for antibody responses by ELISA, as described (Leclerc et al, 1995, Eur. J. Immunol,25, 2533). Briefly, 96 well microplates (Nunc, Roskilde, Denmark) were coated overnight with protein or peptide in 50 mM carbonate buffer. After washes in PBS containing 0.1% Tween 20, diluted sera or culture supernatants were added to the wells and incubated for 1 h at 37° C. Then, goat anti-mouse IgM- or IgG-(Sigma) or IgA-or IgE-(Southern Biotechnology, Birmingham, Ala.) peroxidase conjugates or goat biotinylated anti-mouse IgG1, IgG2a, IgG2b or IgG3 (Amersham, Les Ulis, France) were added for 1 h at 37° C. The binding of biotinylated Ab was detected by streptavidin-horseradish peroxidase. After washing, the substrate solution prepared with o-phenylenediamine (Sigma) and hydrogen peroxide (Sigma)was added to the plates. Optical densities were then read at 492 nm in an ELISA reader (Dynatech, Marnes la Coquette, France). The negative control consisted of either serum from mice immunized with an irrelevant non cross-reactive antigen or of supernatants from cells incubated without antigen. Serum ELISA results are expressed as $\log_{10}$ titer calculated by linear regression analysis plotting dilution versus $A_{492}$ with the titer being defined as the $\log_{10}$ highest dilution which gave twice the absorbance of negative control serum dilution 1/100. Results are given as the arithmetic mean ± standard error of individual sera titers. Statistical analysis was performed by Studen't test and p values of less than 0.05 were considered significant. Antibodies in culture supernatants are expressed as (the optical density of supernatant of cell culture with antigen minus the optical density of supernatant of cell culture without antigen)×100 (ΔOD×1000).

2)Results 2.1 Capacity of particulate antigens to induce antibody production.

The capacity of particulate antigens to induce antibody production has been investigated. For this purpose, five different proteins were covalently linked with glutaraldehyde to 1 μm synthetic microspheres. BALB/c mice were twice immunized with these various proteins linked to beads, without adjuvant, or received the same proteins administered with aluminum hydroxide (alum) as adjuvant. Seric antibody responses were analyzed by ELISA.

Figure 17:
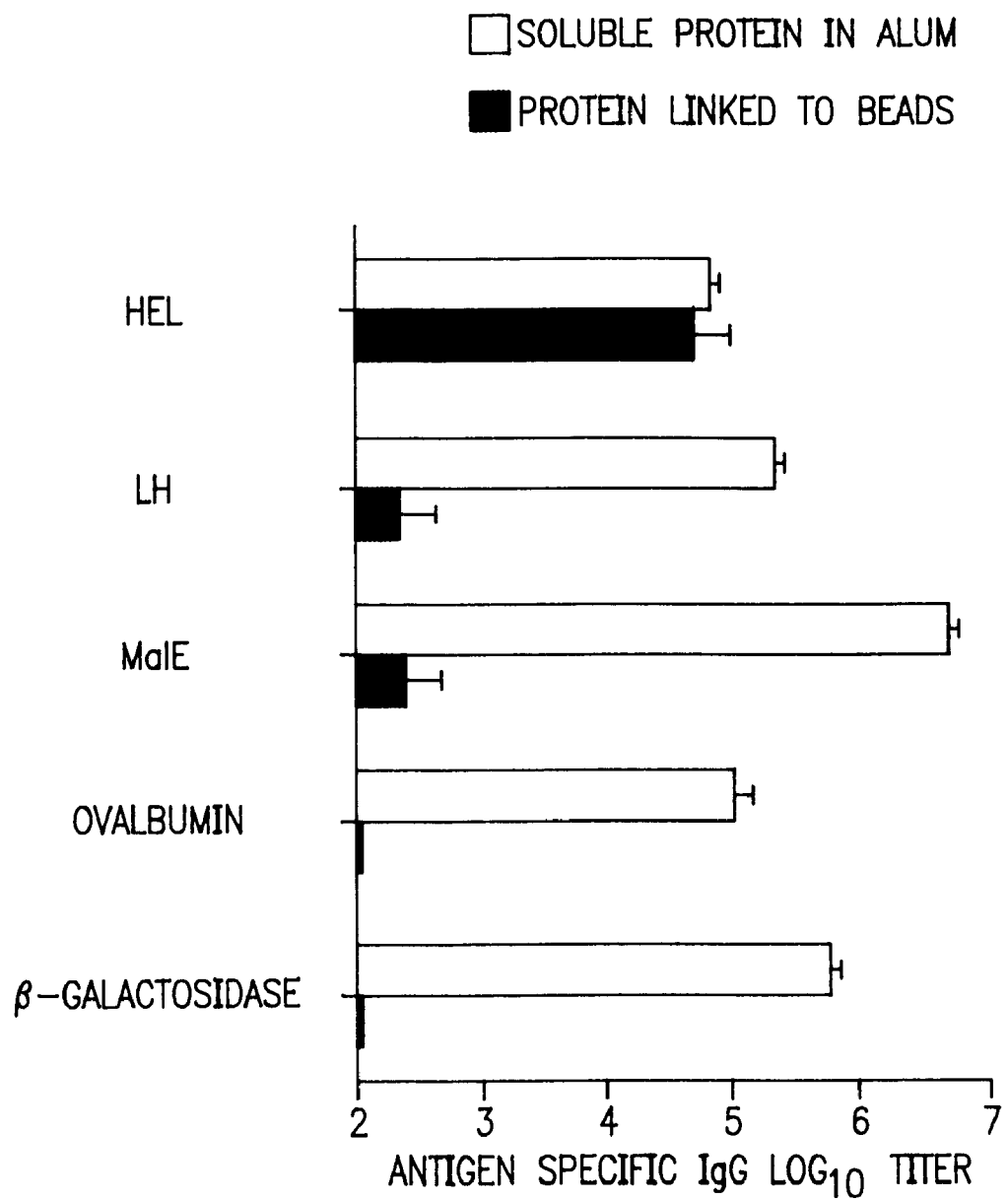

As illustrated in FIG. 17, four out of the five tested proteins linked to beads (hemocyanin, Ma1E, ovalbumin and β-galactosidase) failed to induce antibody production after administration to mice in the absence of adjuvant, while the same proteins injected in alum stimulated high antibody responses. Either IgG (FIG. 17), IgG, IgA or IgE specific antibodies were not detected in sera of mice immunized with these particulate antigens.

In contrast, BALB/c mice receiving two injections of lysozyme (HEL) linked to beads developed a strong antigen-specific antibody response. The level of antibody production induced by particulate HEL was similar to the one induced by soluble HEL in alum. It should be noted that all proteins tested in this experiment were previously shown to induce in vivo CD4+ T cell activation when linked to beads and administered without adjuvant.

These results demonstrate that, in contrast to other proteins, 1-μm particulate HEL has the capacity to stimulate antibody synthesis in vivo, although it has been previously demonstrated that, in vitro, B lymphocytes cannot present this particulate antigen to T cells.

2.2 Characterization of the antibody response elicited by particulate lysozyme.

The characteristics of the antibody response induced in HEL-beads immunized mice was then characterized.

Figure 18A:
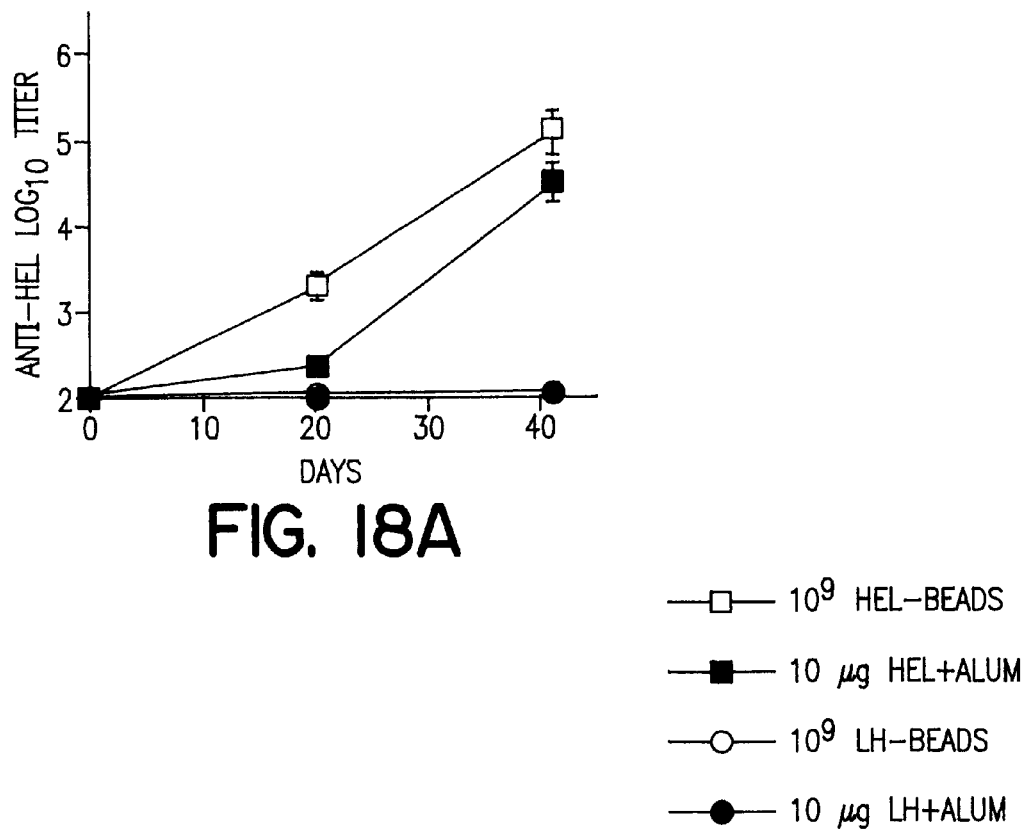
Figure 18B:
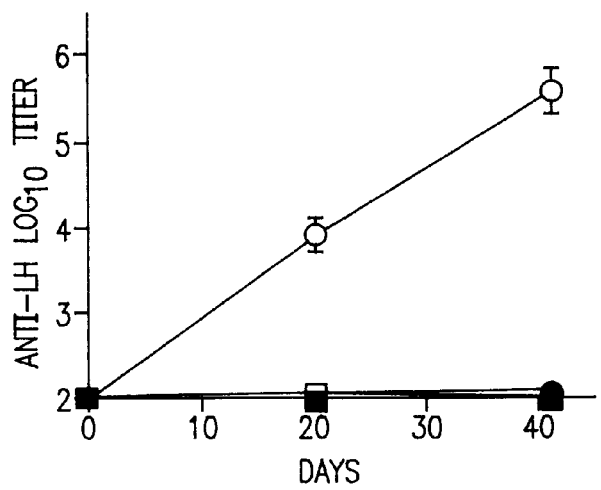

BALI/c mice were injected with equivalent amounts of HEL or hemocyanin (LH) in soluble or particulate form to compare the kinetics of antibody secretion induced by those immunogens. Although the primary response was weaker, the secondary antibody response induced by particulate HEL was comparable to the antibody response developed in mice immunized with HEL in alum (FIG. 18A). These responses were induced with equivalent doses of HEL administered either in soluble (10 μg) or particulate form ($10^9$ HEL-beads corresponding to 10 μg of protein). The antibody production induced by HEL-beads was specific for the protein linked to beads since no cross-reactivity with LH, a heterologous antigen, was observed (FIG. 18B). Moreover, mice injected with LH-beads did not develop anti-HEL IgG antibodies (FIG. 18B) It should be noted that particulate LH failed to induce a specific antibody response (FIG. 18B), as previously shown (FIG. 17), even after administration of lower doses of beads or of LH linked to other types of latex particle which binds antigen without coupling agent. In these experiments, immunization of mice LH-beads stimulated a strong CD4+ T cell proliferative response and spleen cells from these mice produced high levels of IL-2 after in vitro stimulation with LH. Moreover, mice primed with LH-beads prior to subsequent immunization with soluble LH showed an increased anti-LH antibody response, as compared to unprimed mice, indicating that the CD4+ T cells activated by LH-beads could provide strong helper activity to B lymphocytes.

Figure 19:
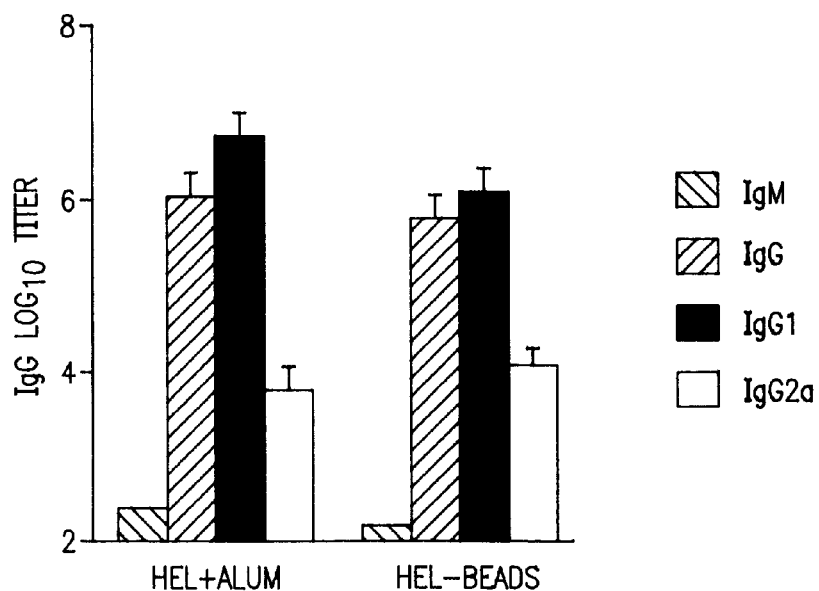

The antibodies produced in response to HEL-beads were of the IgG isotype with very low levels of IgM (FIG. 19) and undetectable levels of IgA and IgE. The pattern of specific antibodies induced by particulate HEL was dominated by IgG1 antibodies with lower IgG2a antibody levels. A similar pattern of isotypes was observed in mice immunized with soluble HEL and alum (FIG. 19). No detectable levels of IgG2b or IgG3 anti-HEL antibodies were produced.

Figure 20:
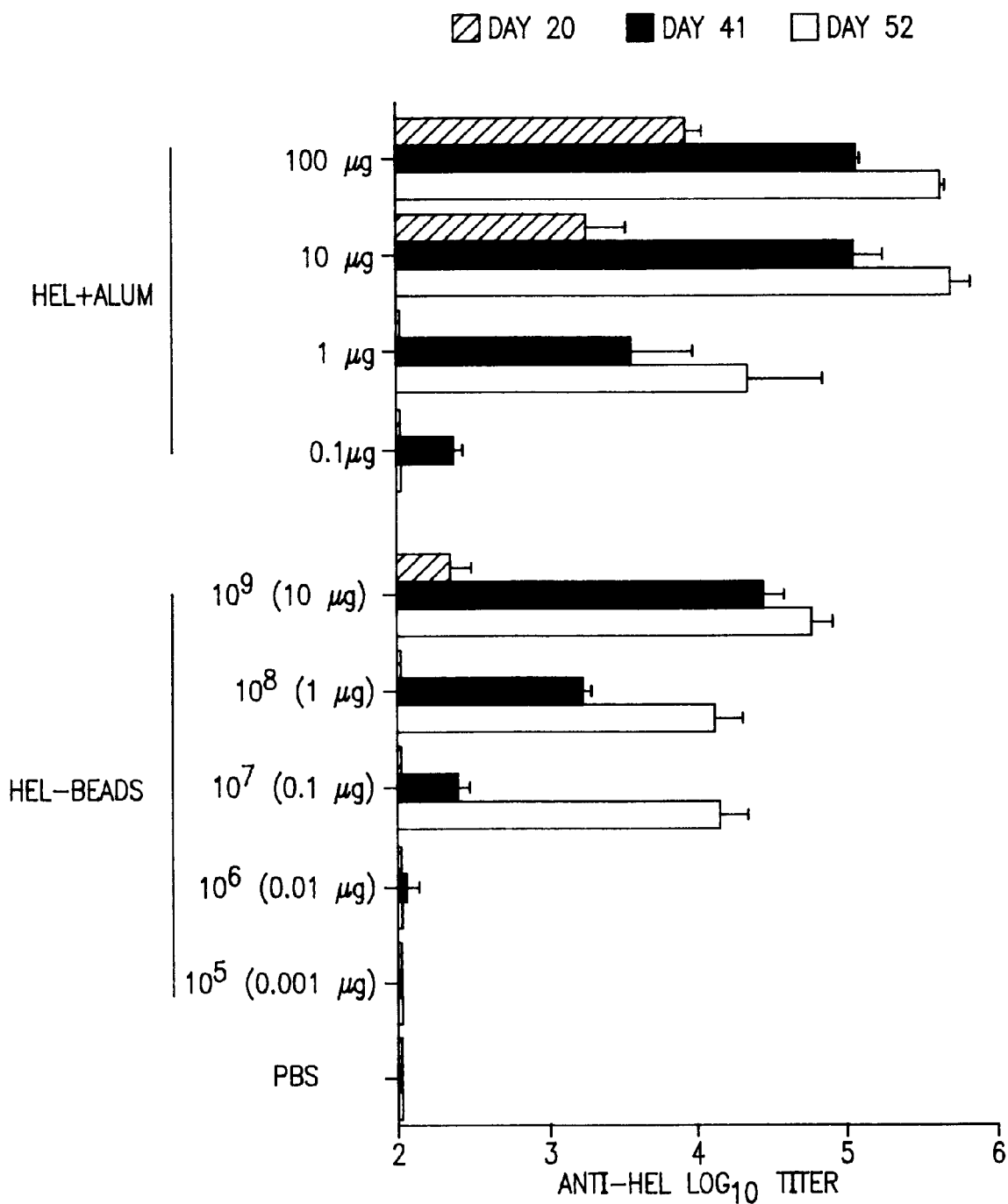

The antibody response of mice injected with various doses of soluble HEL in alum or of HEL-beads was next analyzed. As shown in FIG. 20, one injection of 10 or 100 μg of HEL in alum induced detectable antibody responses whereas two injections of $10^9$ HEL-beads (containing 10 μg of HEL) were required to promote significant anti-HEL antibody production. However, after two or three injections, high levels of antibody responses were observed in mice immunized with $10^9$ or $10^8$ HEL-beads. Moreover, three injections of $10^7$ HEL-beads (corresponding to 0.1 μg of protein)administered without adjuvant induced a high antibody response, whereas HEL in alum was no more immunogenic at this dose. It should be noted that particulate HEL elicited a long-lasting antibody response, since high levels of HEL specific antibodies were still detectable 7 months after immunization with 109 HEL-beads.

2.3 Requirement of CD4± HELPER T cell activity for induction of antibody response by particulate antigens.

To understand the mechanisms responsible for this very efficient anti-HEL antibody response induced by the particulate HEL, the involvement of helper T cells in this antibody response using CD4+ T cell depleted mice was first investigated.

Figure 21:
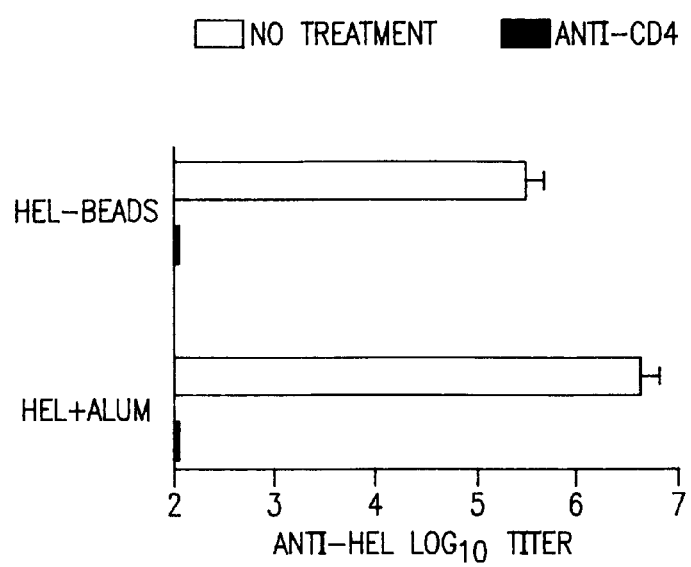

CD4+ T cells were eliminated by treatment of mice with an anti-CD4 monoclonal antibody and CD4+ T cell-depleted BALB/c mice as well as untreated animals, were immunized with HEL-beads or with soluble HEL in alum. Ten days after the last immunization, high levels of anti-HEL antibodies were produced by control mice immunized with HEL-beads whereas neither IgM nor IgG antibodies were detected in CD4+ T cell-depleted mice sera (FIG. 21). Mice immunized with HEL and alum exhibited high antibody responses which were also totally suppressed by anti-CD4 treatment.

The capacity of athymic nude mice to produce anti-HEL antibodies after immunization with particulate HEL was also analyzed. Even after three injections of this antigen, these mice were unable to develop either IgG or IgM specific antibodies, confirming that helper T cells are necessary to stimulate B cell response by particulate HEL. It should be noted that these nude mice were able to produce antibodies in response to TNP-LPS, showing that they were able to respond to a T-independent antigen.

To further analyse the involvement of helper T cells in the activation of antibody response by particulate antigen, synthetic peptides containing either both B- and T-cell epitopes or only a B-cell epitope were covalently linked to particles. Two different antigenic systems were used for these experiments. First, two synthetic peptides from the VP1 protein of the poliovirus type 1 containing either a B-cell epitope alone, C3:B (93–103), or one linked to the poliovirus (103–116) T-cell epitope, C3:BT(93–116) (Van derwerf, 1983, Proc. Natl. Acad. Sci. USA, 80, 5080; Wychowski, 1983, EMBO J., 2, 2019; Leclerc et al., 1991, J. Virol. 65,711)were used. The CD4+ T cell response against the C3:T(103–116) epitope is restricted by $H-2^d$ haplotype and the C3:BT(93–116) peptide was previously shown to induce antibody response after administration in CFA to BALB/c mice. The second system used two synthetic peptides from the PreS region of HBsAg of hepatitis B virus containing either a B-cell epitope alone, PreS:B(132–145), or one linked to the (120–132) T-cell epitope, PreS:TB (120–145) (Milich et al., 1986, J.Exp. Med., 164, 352). The PreS:T (120–132) epitope is immunodominant in the $H-2^q$ haplotype, and the PreS:TB(120–145) peptide injected to DBA/1 mice with alum can trigger strong antibody responses.

Figure 22A:
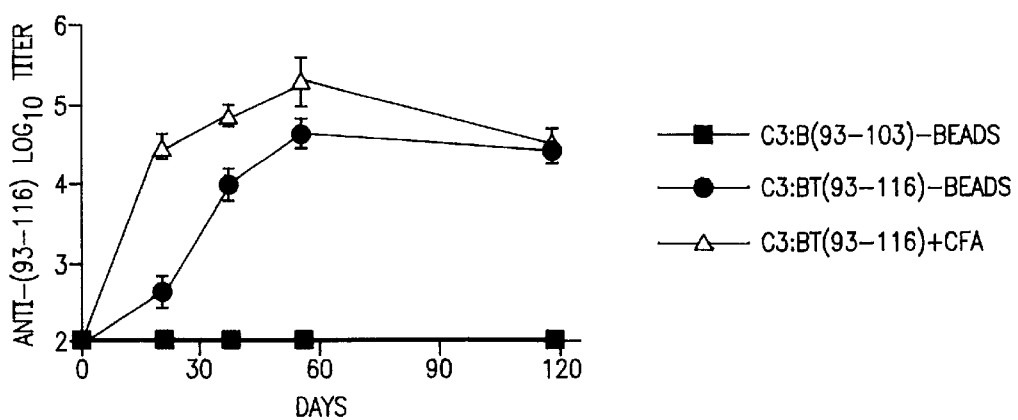
FIGS. 22A and 22B illustrate the antibody induction by a synthetic peptide containing a B-cell epitope bound to synthetic particles respectively in BALB/C (FIG. 22A) and in DBA/1 (FIG. 22B) mice.

BALB/c ($H-2^d$) mice injected with the soluble C3:BT peptide, containing both T- and B-cell epitopes, in adjuvant, developed a strong anti-peptide antibody response (FIG. 22A). Interestingly, immunization of BALB/c mice with the C3:BT peptide linked to beads in the absence of adjuvant also led to high levels of antibody synthesis. It should be noted that the antibody response induced by the particulate C3:BT peptide was comparable to the response obtained after immunization of mice with soluble C3:BT peptide in CFA. The C3 specific antibodies produced after immunization with the C3:TB-beads persisted at least 4 months after the last injection (FIG. 22A). In contrast, a synthetic peptide containing only the C3:B cell epitope, lacking its naturally flanging T cell epitope and linked to beads, failed to induce any IgG, IgM or IgA responses in BALB/c mice.

Figure 22B:
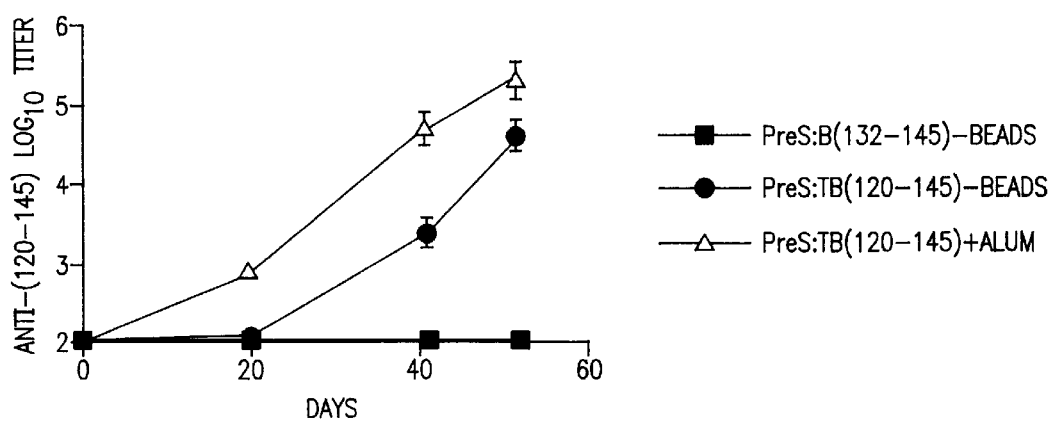

As illustrated in FIG. 22B, DBA/1 mice ($H-2^q$) immunized with the PreS:TB synthetic peptide, containing T- and B-cell epitopes, linked to beads and administered without adjuvant developed a strong peptide specific antibody response, comparable to that induced by the soluble PreS:TB peptide in alum. These results therefore show that short synthetic peptides containing B and T cell epitopes and covalently linked to beads can induce antibody responses.

As described above for the C3:B epitope, immunization of DBA/1 mice with the peptide containing the PreS:B cell epitope alone failed to induce antibody synthesis against this peptide. Moreover, BALB/c mice, which do not respond to the PreS T-cell epitope did not develop any anti-PreS antibody response after repeated immunization with the PreS-TB peptide linked to beads.

Thus, these results clearly demonstrate that the stimulation of antibody synthesis by peptide linked to beads requires the activation of MHC class II-restricted helper T cells.

2.4 Mediation of the cooperation between B and T cells activated by particulate antigen through physical contact via the CD40/CD40L interaction.

To analyse the mechanisms by which these particulate antigens stimulate B cells, an in vitro antibody production assay using the PreS peptide mode has been developed. Splenocytes from PreS:TB peptide immunized DBA/1 mice were stimulated in vitro with the different PreS peptides, in either soluble form or linked to the particles.

Figure 23A:
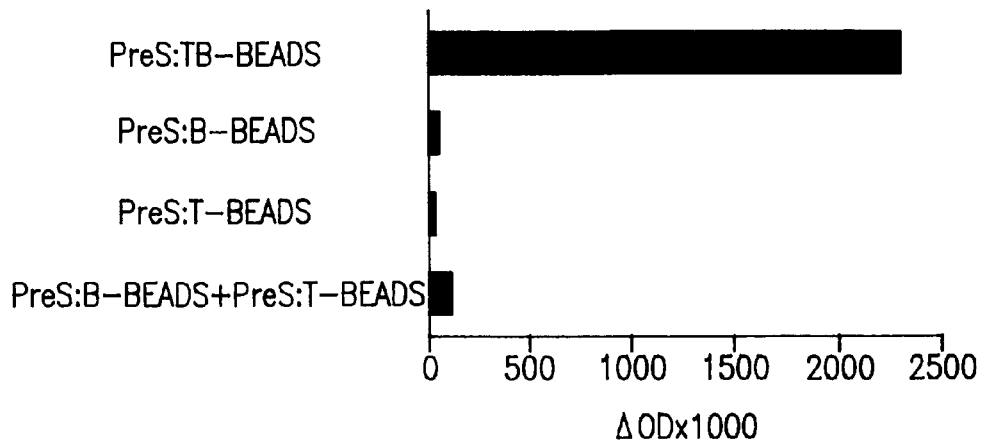
FIGS. 23A and 23B illustrate the in vitro stimulation of antibody responses by peptides comprising B and T cell epitopes linked to beads (FIG. 23A) or not linked (FIG. 23B)
Figure 23B:
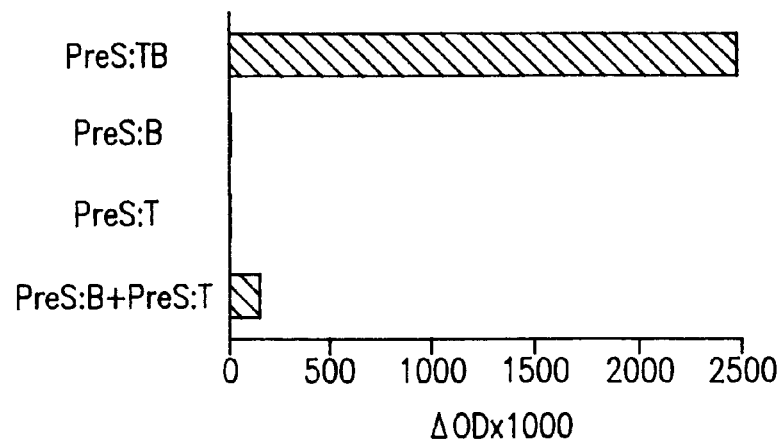

As shown in FIG. 23 and confirming the results obtained in vivo, strong in vitro anti-PreS antibody responses were obtained when splenocytes were stimulated with the peptide containing both B- and T-cell epitopes while no responses were induced by the peptide containing only the B cell epitope. These results were independent of the particulate (FIG. 23A) or soluble (FIG. 23B) form of the antigenic peptide used for in vitro stimulation of the splenocyte cultures. Moreover, the simultaneous addition to the culture of peptides containing B- or T-cell epitope did not stimulate antibody synthesis. Similarly, immune splenocytes were unable to produce anti-PreS antibodies in response to the PreS:B peptide linked to beads in the presence of the PreS:T peptide in either particulate form (FIG. 23A) or soluble form.

To further analyze the mechanisms regulating the induction of antibodies by these peptides linked to 1 $\mu$m beads, the cell cultures were stimulated with these various immunogens in the presence of an anti-CD40 monoclonal antibody which was shown to inhibit the binding of soluble CD40 ligand (CD40L) to soluble CD40 and to cell-surface CD40 molecule. The addition of this anti-CD40 monoclonal antibody (1 $\mu$g/ml) during the in vitro culture of immune splenocytes with the particulate PreS:TB peptide abolished the induction of anti-PreS antibody response (table 1). This inhibition was specific to this monoclonal antibody since the addition of an irrelevant hamster anti-clonotype γδ mAb at 1 $\mu$g/ml did not modify the antibody production stimulated by the particulate PreS:TB peptide (table 1). The addition of this anti-CD40 mAb also led to inhibition of antibodies produced by immune splenocytes stimulated in vitro with the soluble PreS:TB peptide.

TABLE 1

Inhibition by anti-CD40 mAb of the antibody synthesis induced by particulate or soluble peptide

|  | anti-CD40 | | | control mAb |
|---|---|---|---|---|
| in vitro stimulation with: | 0 | 0.01 $\mu$g/ml | 1 $\mu$g/ml | 1 $\mu$g/ml |
| PreS:TB-beads | 808 ± 184 | 899 ± 126 | 30 ± 30 | 963 |
| PreS:TB peptide | 785 ± 207 | 788 ± 450 | 31 ± 21 | 861 |

---

What we claim is:

1. A method of inducing an immune response in warm-blooded animals comprising administering to warm-blooded animals an immune response inducing amount of synthetic biocompatible microparticles carrying on their surface at least one covalently bonded protein, each carrying at least one epitope to induce an humoral or cellular immune response and having an average diameter of between 0.25 µm and 1.5 µm, the molecular weight(s) of the protein(s) on the microparticle surfaces being adjusted to direct the said immune response towards the induction of cellular and/or humoral response.

2. The method of claim 1 of inducing a mainly cellular response in warm-blooded animals comprising administering to warm-blooded animals an immune inducing amount of synthetic microparticles carrying on their surface at least one covalently bonded protein, each carrying at least one epitope to induce an immune response, the molecular weight of the protein(s) on the microparticle surfaces being greater than 30 kD.

3. The method of claim 1 of inducing an humoral and cellular response in warm-blooded animals comprising administering to warm-blooded animals an immune response inducing amount of synthetic biocompatible microparticles carrying on their surface at least one covalently bonded protein or synthetic peptide, the molecular weight(s) being lower than 30 kD, and the proteins or the synthetic peptides comprising B and T epitopes.

4. The method of claim 1 wherein the bond is formed by reaction between the $NH_2$ and/or CO groups of the proteins and the material making up the microparticle.

5. The method of claim 1 wherein the bond between the proteins and the material making up the microparticle is covalent and formed with or without a bridging reagent.

6. The method of claim 5 wherein the bridging reagent is glutaraldehyde or carbodiimide.

7. She method of claim 1 wherein the said microparticles are biocompatible polymers.

8. The method of claim 7 wherein the said polymer is polyacrolein or polystyrene or lactic acid polymers or copolymers of lactic and glycolic acids.

9. The method of claim 1 wherein the microparticles carry on their surface molecules able to activate the immune system.

10. Synthetic biocompatible microparticles carrying on their surface at least one covalently bonded protein or synthetic peptide and having an average diameter between 0.25 µm and 1.5 µm, each carrying at least one epitope to induce an humoral or cellular immune response, the molecular weight(s) of the protein(s) or of the synthetic peptides on the microparticle surfaces being adjusted to direct the said immune response towards the induction of cellular and/or humoral response.

11. The microparticle of claim 10 wherein the molecular weight of the protein(s) is greater than 30 kD.

12. The microparticle of claim 10 wherein the molecular weight of the protein(s) is lower than 30 kD.

13. The microparticle of claim 12 wherein the protein(s) or the synthetic peptides comprise B and T epitopes.

14. The microparticle of claim 10 wherein the bond is formed by reaction between the $NH_2$ and/or CO groups of the proteins and the material making up the microparticle.

15. The microparticle of claim 10 wherein the bond between the proteins and the polymer microparticle is formed by use of a bridging reagent.

16. The microparticle of claim 15 wherein the bridging reagent is glutaraldehyde, or carbodiimide.

17. The microparticle of claim 10 which is composed of a biocompatible polymer.

18. The microparticle of claim 17 wherein the said polymer is poly(acrolein) or polystyrene, a lactic acid polymer or a copolymer of lactic and glycolic acids.

19. The microparticle of claim 10 wherein it carries on its surface molecules able to activate the immune system.

20. The microparticle according to claim 10 wherein said protein comprises the B epitope from the pre-$s_2$ region of the HBo antigen of the viral hepatitis virus.

21. The microparticle according to claim 10 wherein said protein comprises the B epitope of the VP1 protein of the poliomyelitis virus.

22. The microparticle according to claim 10 wherein said protein comprise the B epitope of the gp120 protein of the HIV-1 virus.

23. Pharmaceutical composition wherein it comprises microparticles according to claim 10 in combination with pharmaceutically compatible diluents or adjuvants.

* * * * *